United States Patent
Goto et al.

(10) Patent No.: US 11,530,434 B2
(45) Date of Patent: Dec. 20, 2022

(54) CELL MASS EVALUATION METHOD AND DEVICE FOR ANALYZING STATE OF CELL MASS

(71) Applicant: HAMAMATSU PHOTONICS K.K., Hamamatsu (JP)

(72) Inventors: Kentaro Goto, Hamamatsu (JP); Toyohiko Yamauchi, Hamamatsu (JP); Hidenao Yamada, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 586 days.

(21) Appl. No.: 16/499,957

(22) PCT Filed: Mar. 13, 2018

(86) PCT No.: PCT/JP2018/009720
§ 371 (c)(1),
(2) Date: Oct. 1, 2019

(87) PCT Pub. No.: WO2018/186120
PCT Pub. Date: Oct. 11, 2018

(65) Prior Publication Data
US 2021/0102235 A1    Apr. 8, 2021

(30) Foreign Application Priority Data
Apr. 3, 2017   (JP) .............................. JP2017-073891

(51) Int. Cl.
*G06K 9/00*     (2022.01)
*C12Q 1/24*     (2006.01)
(Continued)

(52) U.S. Cl.
CPC .............. *C12Q 1/24* (2013.01); *G01N 1/2813* (2013.01); *G01N 15/06* (2013.01); *G06T 7/0014* (2013.01);
(Continued)

(58) Field of Classification Search
CPC ............................................ G06T 2207/30024
See application file for complete search history.

(56) References Cited

U.S. PATENT DOCUMENTS

| | | | | |
|---|---|---|---|---|
| 2011/0104744 A1* | 5/2011 | Ozasa | .................. | G01N 15/147 435/39 |
| 2014/0050386 A1* | 2/2014 | Humayun | ............. | G06T 7/0012 382/133 |
| 2015/0111291 A1* | 4/2015 | Aragaki | .................... | G06T 7/20 435/288.7 |

FOREIGN PATENT DOCUMENTS

| JP | 2008-064534 A | 3/2008 |
|---|---|---|
| JP | 2014-016666 A | 1/2014 |

(Continued)

OTHER PUBLICATIONS

International Preliminary Report on Patentability dated Oct. 17, 2019 for PCT/JP2018/009720.
(Continued)

*Primary Examiner* — Hadi Akhavannik
(74) *Attorney, Agent, or Firm* — Faegre Drinker Biddle & Reath LLP

(57) ABSTRACT

An evaluation method is a method for evaluating a cell mass containing a plurality of aggregated cells, and includes an imaging step of capturing an image of light obtained from the cell mass by irradiating the cell mass with light, an analysis step of setting a reference point for the cell mass included in image data obtained by the imaging step, setting sampling circles centered on the reference point, and determining a parameter for a state of the cell mass based on image data included in regions on the sampling circles, and an evaluation step of evaluating the cell mass based on the parameter.

21 Claims, 19 Drawing Sheets

(51) Int. Cl.
  *G01N 1/28* (2006.01)
  *G01N 15/06* (2006.01)
  *G06T 7/00* (2017.01)
(52) U.S. Cl.
  CPC ............... *G01N 2015/0693* (2013.01); *G06T 2207/10048* (2013.01); *G06T 2207/30024* (2013.01)

(56) References Cited

FOREIGN PATENT DOCUMENTS

JP   2016-123366 A   7/2016
WO  WO-2010/146802 A1  12/2010
WO  WO-2011/043077 A1  4/2011

OTHER PUBLICATIONS

M. Amit et al., "Suspension Culture of Undifferentiated Human Embryonic and Induced Pluripotent Stem Cells," Stemm Cell Reviews and Reports, vol. 6, No. 2, 2010, pp. 248-259.
P. Yu et al., "Holographic optical coherence imaging of tumor spheroids," Applied Physics letters, vol. 83, No. 3, 2003, pp. 575-577.
K. Arai et al., "A Novel High-Throughput 3D Screening System for EMT Inhibitors: A Pilot Screening Discovered the EMT Inhibitory Activity of CDK2 Inhibitor SU9516," PLOS ONE, 2016, pp. 1-18.

* cited by examiner (a)

(b)

(a)

(b)

(a)

(b)

(a)

(b)

(a)

(b)

(a)

(b)

(a)

(b)

(a)

(b)

(a)

(b)

CELL MASS EVALUATION METHOD AND DEVICE FOR ANALYZING STATE OF CELL MASS

TECHNICAL FIELD

The present disclosure relates to a cell mass evaluation method and a cell mass state analysis apparatus.

BACKGROUND ART

Patent Document 1 discloses a method of determining a multi-layer state of a cell mass. In the method described in this document, a first image and a second image in which the same cell mass is imaged with a predetermined time interval are acquired. Further, based on an intensity distribution of a local region in the cell mass of the first image, a block matching of the intensity distribution is performed for the vicinity including the corresponding position in the cell mass of the second image, and a degree of approximation of a region with the highest matching is taken as a representative degree of approximation at the position. The representative degrees of approximation for respective portions of the cell mass are calculated while moving the local region in the first image, and the multi-layer state of the cell mass is determined according to the calculated representative degrees of approximation for respective portions of the cell mass.

Patent Document 2 discloses a method of identifying undifferentiated pluripotent stem cells. In the method described in this document, identification of a colony is performed by a captured image of a colony containing pluripotent stem cells. Specifically, based on an intensity in the captured image, a differentiated colony containing differentiated pluripotent stem cells and an undifferentiated colony containing only undifferentiated pluripotent stem cells are identified.

CITATION LIST

Patent Literature

Patent Document 1: International Publication No. 2010/146802
Patent Document 2: International Publication No. 2011/043077

Non Patent Literature

Non-Patent Document 1: Michal Amit, et al., "Suspension Culture of Undifferentiated Human Embryonic and Induced Pluripotent Stem Cells", Stem Cell Reviews and Reports, Vol. 6, 2, pp. 248-259, (2010)
Non-Patent Document 2: P. Yu, et al., "Holographic optical coherence imaging of tumor spheroids", Applied Physics letters, Vol. 83, 3, pp. 575-577, (2003)
Non-Patent Document 3: Kazuya Arai, et al., "A Novel High-Throughput 3D Screening System for EMT Inhibitors: A Pilot Screening Discovered the EMT Inhibitory Activity of CDK2 Inhibitor SU9516", PLOS ONE, pp. 1-18, Sep. 13, 2016

SUMMARY OF INVENTION

Technical Problem

In the field of bio and regenerative medicine, research using cell masses is actively conducted, and in particular, application to the mass culture, the drug screening and the like is expected. Further, in order to identify usable cell masses, a technique for analyzing and evaluating the state of cell masses is required. For example, the cell mass can be imaged while irradiating the cell mass with light, and the state of the cell mass can be evaluated based on the obtained image (see, for example, Patent Documents 1 and 2). However, usually, the shape of the cell mass is nearly spherical in three dimensions. Therefore, it is not easy to accurately evaluate the state of the cell mass based on a two-dimensional image.

An object of embodiments is to provide a cell mass evaluation method and a cell mass state analysis apparatus capable of more accurately evaluating a state of a cell mass based on an image.

Solution to Problem

An embodiment of the present invention is a cell mass evaluation method. The evaluation method is a method for evaluating a cell mass containing cells aggregated with each other, and includes an imaging step of capturing an image of light obtained from the cell mass by irradiation with light to the cell mass, an analysis step of setting a reference point for the cell mass included in the image obtained by the imaging step, setting a sampling circle centered on the reference point, and determining a parameter for a state of the cell mass based on image data included in a region on the sampling circle, and an evaluation step of evaluating the cell mass based on the parameter.

Further, an embodiment of the present invention is a cell mass state analysis apparatus. The state analysis apparatus is an apparatus used for evaluating a cell mass containing cells aggregated with each other, and includes a light source for outputting light with which the cell mass is irradiated, an imaging unit for capturing an image of light obtained from the cell mass by irradiation with the light, and an analysis unit for setting a reference point for the cell mass included in the image obtained by the imaging, setting a sampling circle centered on the reference point, and determining a parameter for a state of the cell mass based on image data included in a region on the sampling circle.

In the above evaluation method and the state analysis apparatus, an image including a cell mass is acquired by capturing an image of light obtained from the cell mass by light irradiation in the imaging step or by the imaging unit. Further, in the analysis step, or by the analysis unit, a reference point is set for the cell mass included in the image, and a sampling circle centered on the reference point is set. As the reference point, for example, a point near the center of the cell mass in the image is selected.

According to the findings of the inventors, the state of cells (for example, differentiated/undifferentiated state of stem cells or necrotic state of cancer cells) changes from near the center toward the periphery, and the state of the change is approximately uniform at positions which are equally distant from near the center. That is, the parameter related to the state of the cell mass can be determined based on the image data extracted from a region in which the state of cells is substantially uniform. Therefore, according to the above evaluation method and the state analysis apparatus, the state of the cell mass can be more accurately evaluated based on the image.

Advantageous Effects of Invention

According to the cell mass evaluation method and the cell mass state analysis apparatus of the embodiments, the state of the cell mass can be more accurately evaluated based on the image.

DESCRIPTION OF EMBODIMENTS

Hereinafter, embodiments of a cell mass evaluation method and a cell mass state analysis apparatus will be described in detail with reference to the accompanying drawings. In the description of the drawings, the same elements will be denoted by the same reference signs, without redundant description.

Figure 1:
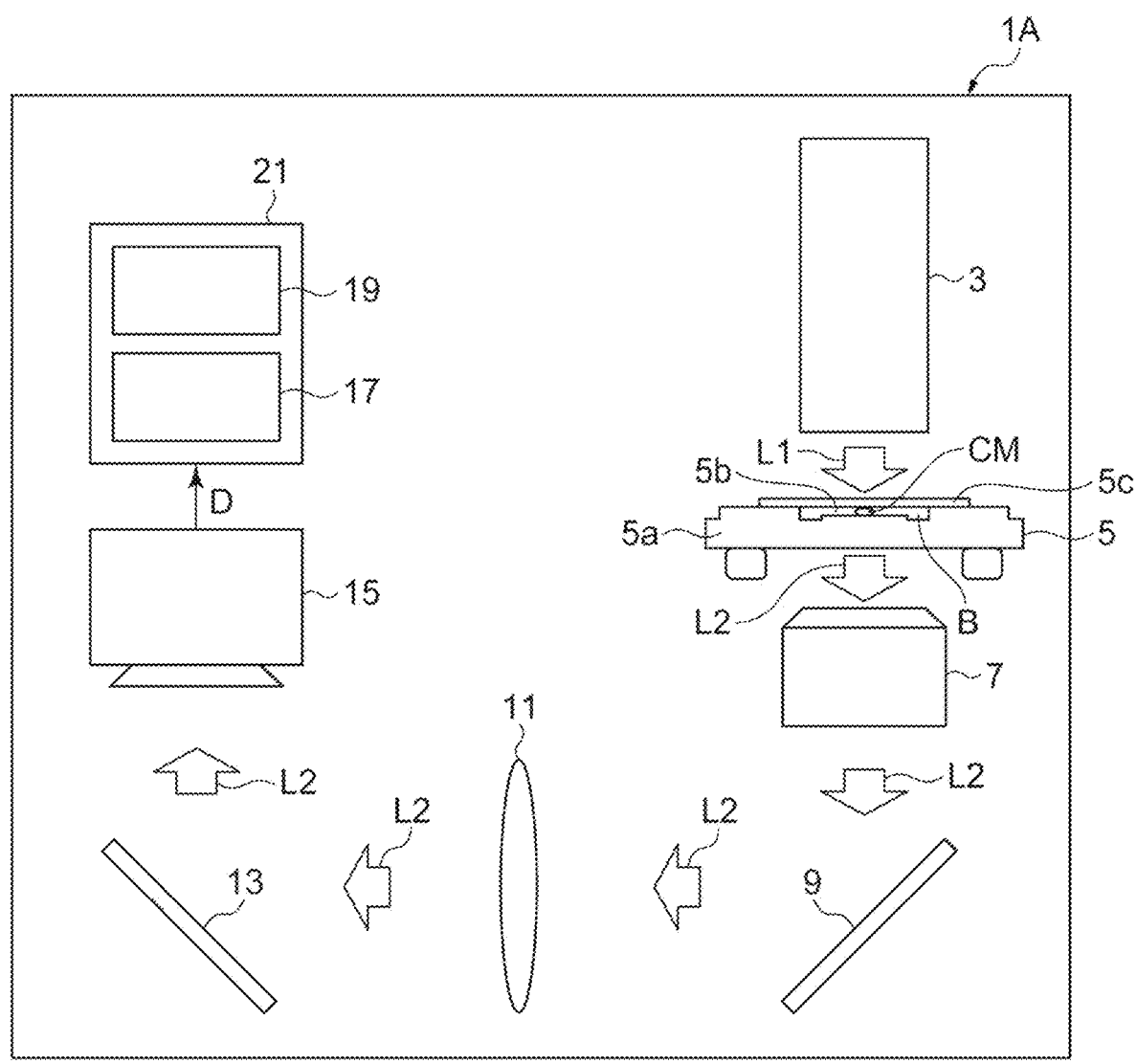
FIG. 1 is a diagram schematically illustrating a configuration of a state analysis apparatus according to an embodiment.

FIG. 1 is a diagram schematically illustrating a configuration of a state analysis apparatus 1A according to an embodiment. The state analysis apparatus 1A of the present embodiment is an apparatus used for evaluating a cell mass CM containing cells aggregated with each other. The cell mass CM is constituted by stem cells such as iPS cells and ES cells, or cells such as cancer cells. As illustrated in FIG. 1, the state analysis apparatus 1A includes a light source 3, a holding unit 5, an objective lens 7, a first reflecting mirror 9, a focusing lens 11, a second reflecting mirror 13, an imaging unit 15, an analysis unit 17, and an evaluation unit 19.

The light source 3 outputs light L1 with which the cell mass CM is irradiated. The light L1 is, for example, infrared light, and its suitable wavelength is, for example, 0.95 μm to 1.7 μm. In one example, the light source 3 includes a semiconductor laser element, and the light L1 for irradiating the cell mass CM is coherent laser light. Further, the light L1 is continuous light (CW light).

The holding unit 5 is a container for holding the cell mass CM in a state of being immersed in a culture solution B. The holding unit 5 of the present embodiment holds the cell mass CM in a state of being crushed into a thin layer shape. In addition, the cell mass CM before being crushed is substantially spherical, and its diameter is, for example, 20 μm to 400 μm.

The holding unit 5 of the present embodiment has a main portion 5a and a lid portion (cover glass) 5c. The main portion 5a is a container having a shallow bottom, and includes a depressed portion 5b for housing the cell mass CM. The lid portion 5c is a flat plate shaped member placed on the main portion 5a and sealing the opening of the depressed portion 5b from above. The bottom surface of the depressed portion 5b and the back surface of the lid portion 5c facing each other are parallel and flat with high accuracy. The main portion 5a and the lid portion 5c are transparent for the light output from the light source 3. The constituent material of the main portion 5a and the lid portion 5c is, for example, quartz glass.

The distance between the bottom surface of the depressed portion 5b and the lid portion 5c (in other words, the depth of the space for housing the cell mass CM) is, for example, 10 μm or more, and 350 μm or less. In one example, the distance is 100 μm. The cell mass CM is crushed by the bottom surface of the depressed portion 5b and the lid portion 5c. Therefore, the thickness of the crushed cell mass CM is equal to the distance between the bottom surface of the depressed portion 5b and the lid portion 5c. As the holding unit 5, for example, a hemocytometer is suitably used. The holding unit 5 is optically coupled to the light source 3 through an optical system which is not shown, and the cell mass CM housed in the depressed portion 5b is irradiated with the light L1 from the thickness direction through the lid portion 5c.

The objective lens 7 is a convex lens for extracting light L2 (for example, transmitted light, reflected light, fluorescence, scattered light, or the like) obtained from the cell mass CM by irradiation with the light L1. The objective lens 7 is optically coupled to the holding unit 5. The objective lens 7 is disposed in the thickness direction of the cell mass CM, and the optical axis thereof coincides with the thickness direction. The objective lens 7 may be disposed opposite to the light irradiation side of the holding unit 5 (that is, the lower surface side of the main portion 5a) as illustrated in FIG. 1, or may be disposed on the light irradiation side of the holding unit 5 (that is, the lid portion 5c side).

The focusing lens 11 is disposed on the optical path between the objective lens 7 and the imaging unit 15, and focuses the light L2 obtained from the cell mass CM to the imaging unit 15. In addition, in the example illustrated in FIG. 1, the reflecting mirror 9 is provided on the optical path between the focusing lens 11 and the objective lens 7, and the optical path of the light L2 is bent. Further, the reflecting mirror 13 is provided on the optical path between the focusing lens 11 and the imaging unit 15, and the optical path of the light L2 is bent again. The reflecting mirrors 9 and 13 are an example of an optical system between the objective lens 7 and the imaging unit 15, and the optical system may be appropriately changed.

The imaging unit 15 is a camera for capturing an image of the light L2 obtained from the cell mass CM by irradiation with the light L1. For example, the imaging unit 15 is a camera having an imaging plane including a plurality of pixels and having an image sensor for generating an electric signal corresponding to the light intensity of the light L2 for each pixel. Further, the imaging unit 15 outputs image data D which is the generated electric signal group. The imaging unit 15 is sensitive to the wavelength of the light L2. When the light L1 is infrared light and the light L2 is transmitted light or reflected light, the imaging unit 15 is sensitive to the infrared region. The camera which is sensitive to the infrared region is, for example, an InGaAs camera sensitive to wavelengths of 900 nm to 1600 nm.

The analysis unit 17 and the evaluation unit 19 are implemented by a computer 21. The computer 21 has a CPU and a memory, and operates by executing a program. The computer 21 is, for example, a personal computer, a smart device, a microcomputer, a cloud server, or the like. The analysis unit 17 and the evaluation unit 19 may be implemented by one computer or may be implemented by separate computers.

The analysis unit 17 determines a parameter for the state of the cell mass CM based on the image data D from the imaging unit 15. The parameter is, for example, the cell number density (the number of cells per unit length, the value including the cell number density in the thickness direction) on the sampling circle set for the cell mass CM. The evaluation unit 19 evaluates the state of the cell mass CM based on the parameter output from the analysis unit 17. For example, when the object is the cell mass CM constituted by a plurality of stem cells, the degree of differentiation of the cell mass is evaluated. Specifically, whether the undifferentiated state is maintained is evaluated for mass culture of cells. Further, when differentiation is induced, whether the cells are differentiated without any problem is evaluated. Further, when the object is the cell mass CM constituted by a plurality of cancer cells, the state of the cell mass (for example, the necrotic state of cancer cells) is evaluated.

Figure 2:
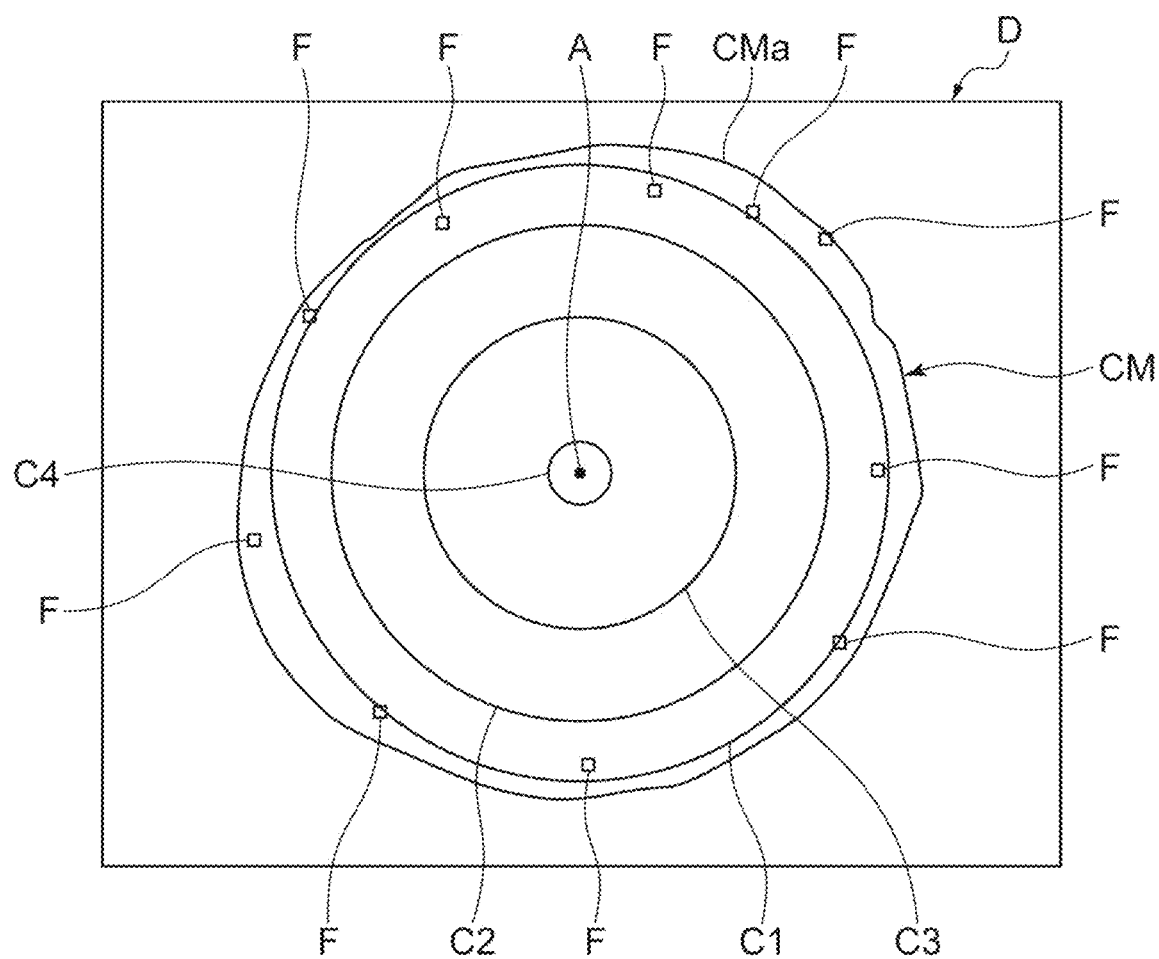
FIG. 2 is a diagram schematically illustrating an example of image data output from an imaging unit.

Next, the parameter calculation method by the analysis unit 17 will be described in detail. FIG. 2 is a diagram schematically illustrating an example of the image data D output from the imaging unit 15. The image data D includes the imaged cell mass CM. The cell mass CM, which is substantially spherical, is crushed, so that its planar shape is substantially circular. The refractive indices are different between the cell mass CM and the surrounding medium (culture solution B), and further, scattering occurs inside the cell mass CM, so that a contour CMa of the cell mass CM clearly appears in the image data D.

The analysis unit 17 sets a reference point A for one cell mass CM included in the image data D. The reference point A is, for example, the central point of the cell mass CM in the image data D. In addition, in this case, the reference point A does not have to be a central point in a strict sense, and may be located near an approximate central point. In many cases, since the contour of cell mass CM in the image data D is not strictly circular, it is necessary to devise a method when finding a central point of the cell mass CM. For example, as illustrated in FIG. 2, the analysis unit 17 selects a plurality of arbitrary points F in the vicinity of the contour inside of the cell mass CM with intervals in the circumferential direction. Further, the analysis unit 17 calculates a point at which distances from the respective points F are substantially equal. For example, the least square center method may be applied to this calculation. The analysis unit 17 sets, for example, a point (an approximate central point of the cell mass CM) obtained in this manner as the reference point A.

Next, the analysis unit 17 sets a plurality of sampling circles centered on the common reference point A for the cell mass CM in the image data D. For example, FIG. 2 illustrates an example in which four sampling circles C1 to C4 centered on the common reference point A are set. The radii of the sampling circles C1 to C4 are different from each other. The radius of the largest sampling circle C1 can be calculated, for example, using a calculation method such as the simple average, the root mean square, or the least square center method for the distances between the reference point A and the plurality of points F. Further, the radius of the other sampling circle is determined by multiplying the radius of the largest sampling circle C1 by a predetermined ratio. For example, the radii of the sampling circles C2 to C4 in FIG. 2 are obtained by multiplying the radius of the sampling circle C1 by 0.8, 0.5 and 0.1, respectively.

Subsequently, the analysis unit 17 determines a plurality of parameters for the state of the cell mass CM based on the image data included in the regions on the plurality of sampling circles. In the example illustrated in FIG. 2, four parameters are determined respectively based on the image data included in the regions on the four sampling circles C1 to C4. The parameter is not particularly limited as long as it relates to the state of the cell mass CM, and is, for example, the cell number density.

For example, in iPS cells or ES cells, when the state of stem cells changes (for example, changes from undifferentiated state to differentiated state), individual cell morphology changes and the cell number density of the cell mass changes. Therefore, by determining the cell number density in the region on the sampling circle of the cell mass CM, it is possible to accurately evaluate the degree of differentiation of respective stem cells located in the region on the sampling circle. Further, when the state of the cell mass CM is deteriorated, the cell mass CM collapses, and before the cell mass CM collapses, variation in cell number density occurs. Therefore, the degree of deterioration of the cell mass CM can be accurately evaluated by determining the cell number density in the region on the sampling circle of the cell mass CM.

According to the findings of the inventors, the index value for the cell number density can be easily obtained by the following calculation. The following Formula (1) is a formula for obtaining an autocorrelation function of the intensity value on the sampling circle.

[Formula 1]

$$RO_{OD}(\Delta r') = \sum_{r=1}^{n/2} \{(f(r) - \mu) \cdot (f(r + \Delta r') - \mu)\} \quad (1)$$

$(\Delta r' = r - r')$ $R_{OD}(\Delta r') = RO_{OD}(\Delta r') / RO_{OD}(0)$

Here, r and r' are pixel numbers sequentially given along the circumferential direction to respective pixels on the sampling circle. f(r) is a pixel value (that is, intensity) at the pixel number r. μ is an average value. n is the number of data on the sampling circle. Δr' is the difference between r and r'.

Figure 3:
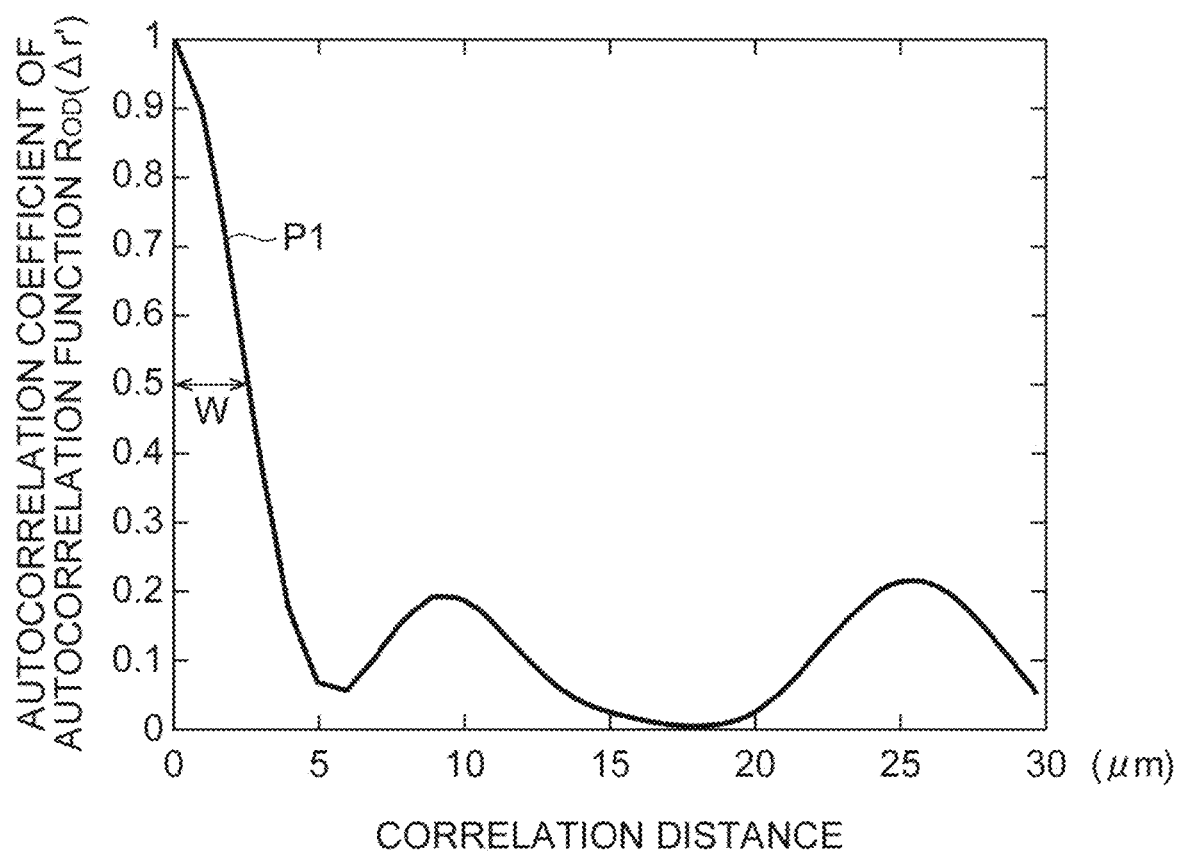
FIG. 3 is a graph illustrating an example of an autocorrelation function for a certain sampling circle.

FIG. 3 is a graph illustrating an example of the autocorrelation function for a certain sampling circle, which is calculated by Formula (1). The horizontal axis represents the correlation distance, and the vertical axis represents the autocorrelation coefficient of the autocorrelation function $R_{OD}(\Delta r')$. The analysis unit 17 determines the width W of the first waveform P1 of the autocorrelation function (the width at a value of 1/N of the maximum value of the autocorrelation coefficient (N>1), for example, in the case of N=2, the width at half the maximum value). The width W is an index value of the cell number density, and is related to the cell number density on the sampling circle of the cell mass.

That is, the width W represents a cycle of intensity in the image data, and when the cell number density is large (cells are densely packed), the cycle of intensity in the image data is short, so that the width W is small. On the other hand, when the cell number density is small, the cycle of intensity in the image data is long, so that the width W is large. Therefore, the cell number density in each of the sampling circles C1 to C4 can be estimated and compared by determining the width W for each of the sampling circles C1 to C4. For example, by comparing the widths W calculated for the sampling circles C1 to C4 with each other, it is possible to find how the cell number density changes according to the distance from the central point of the cell mass CM. In addition, the analysis unit 17 may use the width W as the parameter for the state of the cell mass CM. In the following description, the width W may be referred to as an "autocorrelation distance".

The evaluation unit 19 evaluates the degree of differentiation of the cell mass CM based on the parameter determined by the analysis unit 17. As described above, in some types of cells, when the state of stem cells changes from an undifferentiated state to a differentiated state, the cell number density of the cell mass changes. Therefore, the cell state of the cell mass CM can be determined by evaluating the degree of differentiation of stem cells in the cell mass CM from the cell number densities obtained for the sampling circles C1 to C4. The evaluation unit 19 causes the display device (display) coupled to the computer 21 to display the obtained result, for example.

Figure 4:
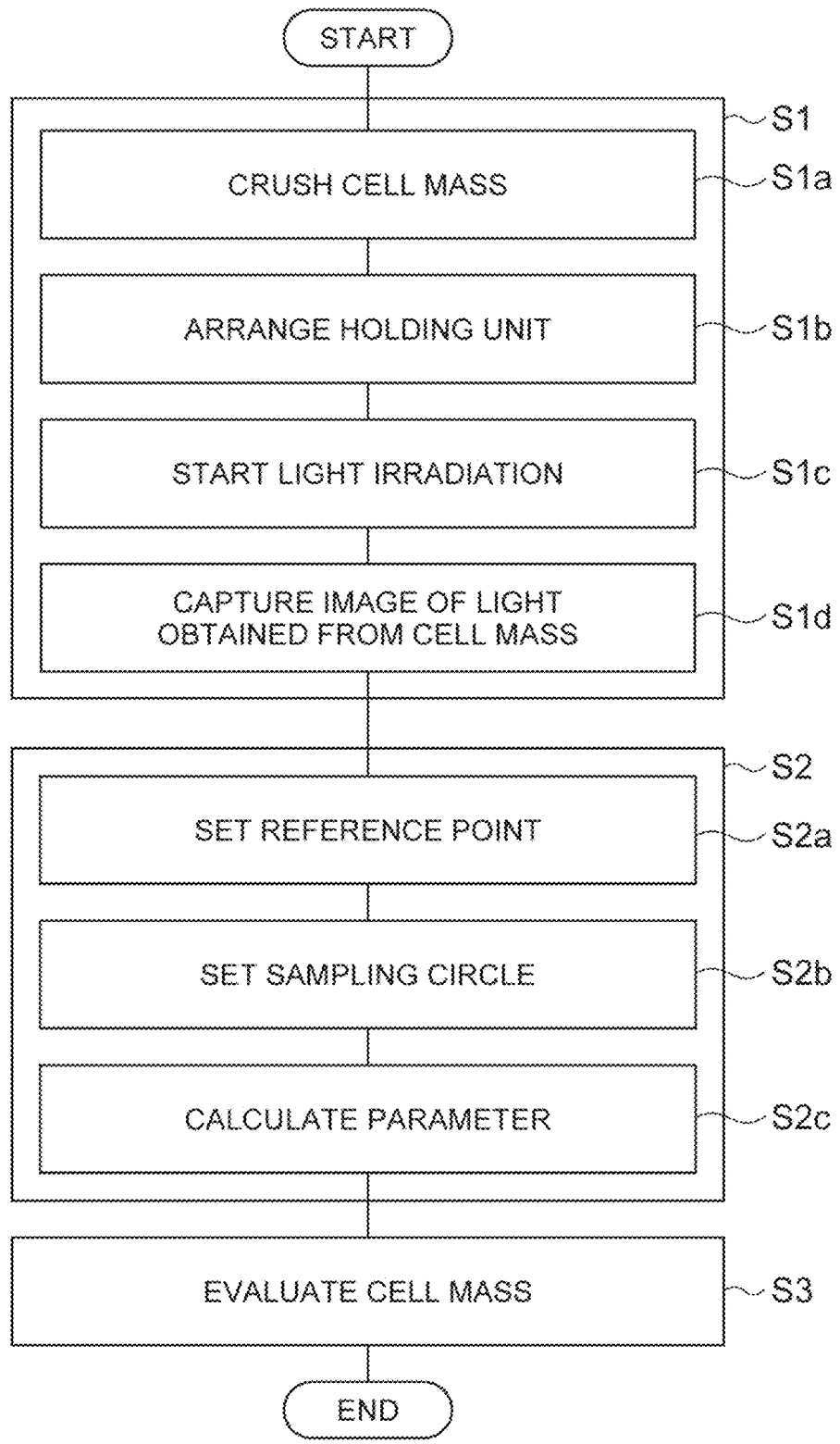
FIG. 4 is a flowchart illustrating an evaluation method of a cell mass CM according to an embodiment.

Next, an evaluation method of the cell mass CM according to an embodiment will be described. FIG. 4 is a flowchart illustrating a method of evaluating the cell mass CM according to the present embodiment. This evaluation method is a method of evaluating the cell mass CM containing a plurality of aggregated stem cells, and is suitably carried out using, for example, the state analysis apparatus IA described above.

First, the cell mass CM to be evaluated is irradiated with light, and light L2 obtained from the cell mass CM by light irradiation is imaged (step S1, imaging step). Specifically, first, the cell mass CM to be evaluated is housed in the depressed portion 5b of the holding unit 5, and the cell mass CM is crushed into a thin layer shape by applying pressure from above through the lid portion 5c (step S1a). Next, by arranging the holding unit 5 between the light source 3 and the objective lens 7, the upper surface side of the holding unit 5 and the light source 3 are optically coupled, and the back surface side of the holding unit 5 and the objective lens 7 are optically coupled (step S1b).

Subsequently, irradiation of the cell mass CM with the light L1 is started (step S1c). This light irradiation is performed by the light source 3, and the light L1 is, for example, infrared light and continuous light. Further, at this time, the cell mass CM is irradiated with the light L1 in the thickness direction. Subsequently, the light L2 obtained from the cell mass CM by the light irradiation is imaged (step S1d). As described above, the light L2 obtained from the cell mass CM is, for example, transmitted light, reflected light, or fluorescence. In step S1d, the imaging unit 15 generates the image data D.

Subsequently, based on the image data D obtained by the imaging, the parameter for the state of the cell mass CM is determined (step S2, analysis step). This step S2 is performed by, for example, the analysis unit 17. Specifically, first, the reference point A is set for one cell mass CM included in the image data D (step S2a, see FIG. 2). Next, a first sampling circle and a second sampling circle which are different in radius and centered on the common reference point A are set for the cell mass CM (step S2b). In this embodiment, four sampling circles C1 to C4 (see FIG. 2) are set. Further, based on the image data included in the regions on the sampling circles C1 to C4, four parameters for the state of the cell mass CM are determined (step S2c). The parameter is, for example, the cell number density in each of the sampling circles C1 to C4. Further, the parameter may be the width W (see FIG. 3) of the first waveform P1 of the autocorrelation function of the image data along the circumferential direction of each of the sampling circles C1 to C4.

Finally, the cell mass CM is evaluated based on the four parameters obtained in step S2 (step S3, evaluation step). When the parameter obtained in the previous step S2 is the cell number density or the width W of the first waveform P1, the degree of differentiation of the cell mass CM can be evaluated in this step S3. For example, the degree of differentiation of the cell mass CM can be found by comparing the parameters calculated for the sampling circles C1 to C4 with each other. This step S3 may be performed by, for example, the evaluation unit 19, or may be performed by the observer.

The effects obtained by the evaluation method and the state analysis apparatus 1A of the present embodiment described above will be described.

As described above, in the evaluation method and the state analysis apparatus 1A of the present embodiment, the image data D including the cell mass CM is acquired by imaging the light L2 obtained from the cell mass CM by light irradiation. Further, the reference point A is set for the cell mass CM included in the image data D, and the sampling circles C1 to C4 centered on the reference point A are set. As the reference point A, for example, one point near the center of the cell mass CM in the image data D is selected.

According to Non-Patent Document 1, the state of stem cells (for example, differentiated/undifferentiated state) changes from near the center toward the periphery, and the state of the change is substantially uniform at positions which are equally distant from near the center. That is, the parameter for the state of the cell mass CM can be determined based on the image data extracted from a region in which the state of stem cells is substantially uniform. Further, according to Non-Patent Document 2, the cell mass constituted by a plurality of cancer cells has the state which changes from the center, and the state of the change is uniform at positions which are equally distant from near the center. That is, the parameter for the state of the cell mass CM can be determined based on the image data extracted from a region in which the state of cancer cells is substantially uniform. Therefore, according to the present embodiment, the state of the cell mass CM can be more accurately evaluated based on the two-dimensional image data D.

Further, in the case where the cell mass CM at the time of imaging is spherical, the thickness of the cell mass CM on the circle is almost even when drawing the circle centered on one point near the center of the cell mass CM. Therefore, the parameter calculation accuracy can be enhanced by obtaining the parameter from the pixel data on the sampling circles C1 to C4.

Figure 5:
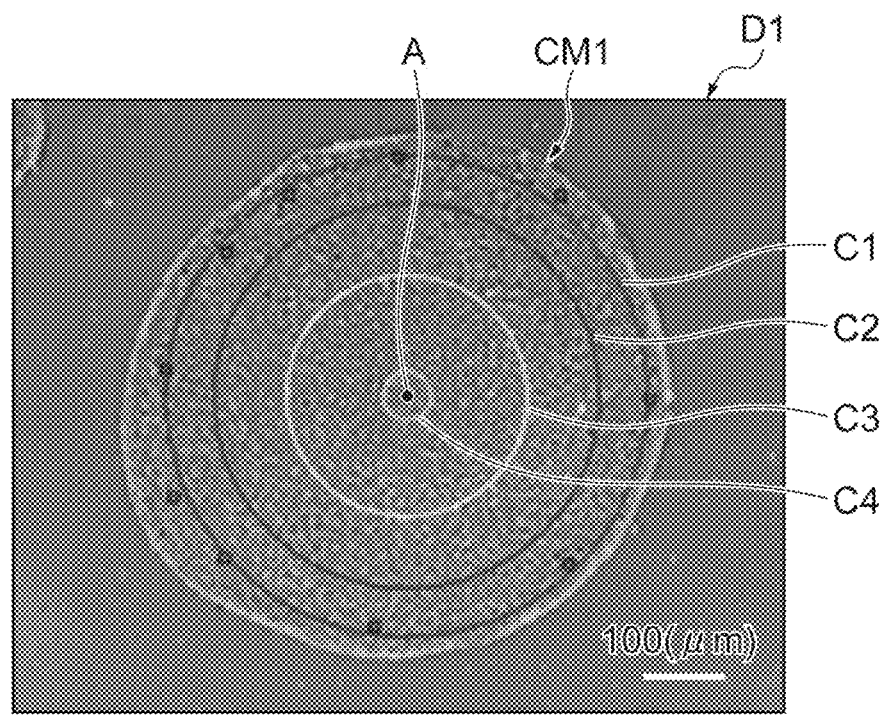
FIG. 5 includes (a), (b) images illustrating a state in which a plurality of sampling circles are set for image data of a cell mass.
Figure 5:
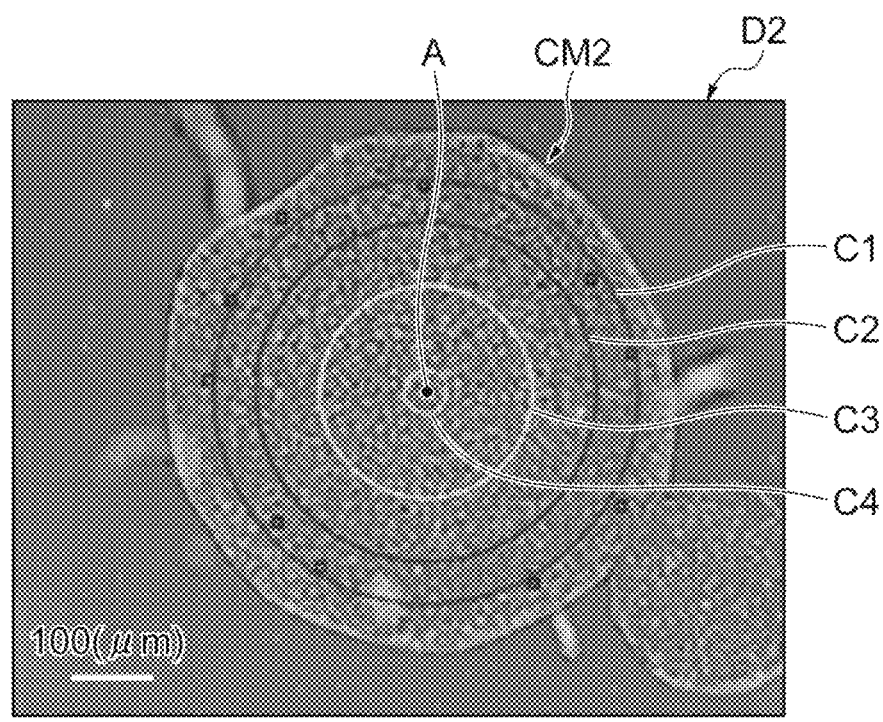
Figure 6:
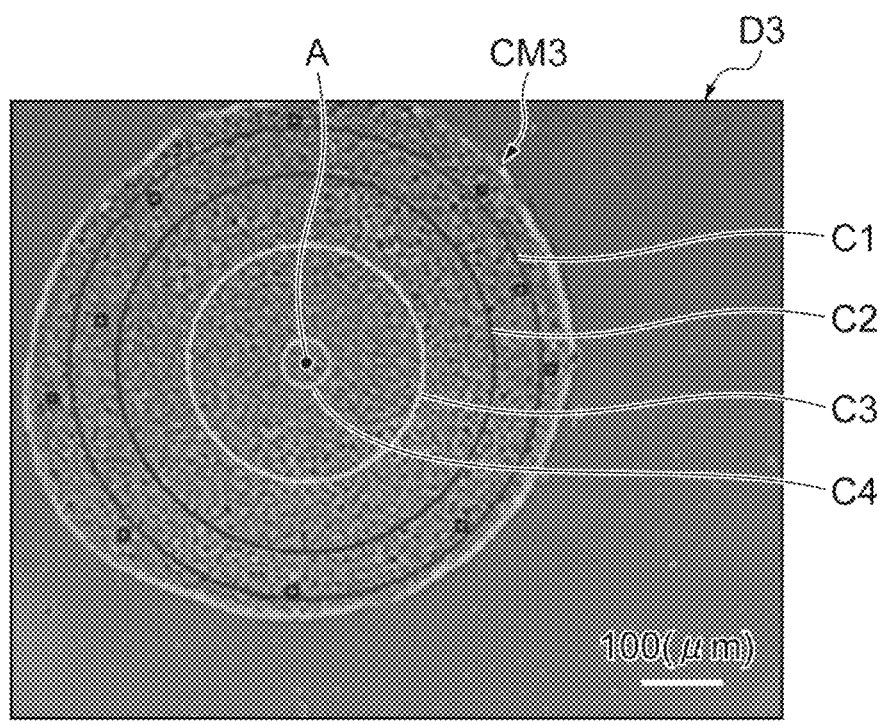
FIG. 6 includes (a), (b) images illustrating a state in which a plurality of sampling circles are set for image data of a cell mass.
Figure 6:
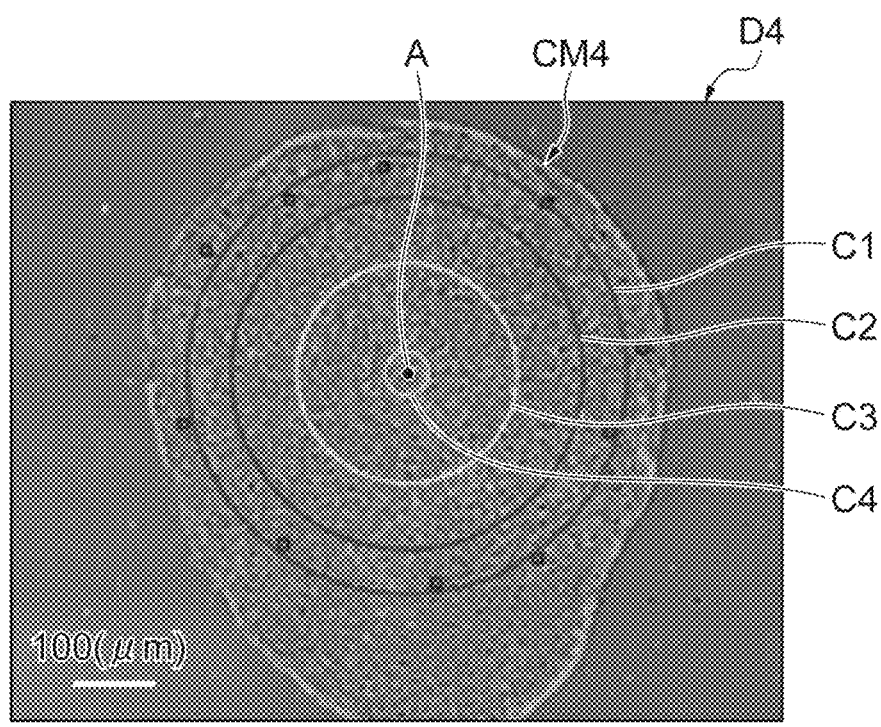
Figure 7:
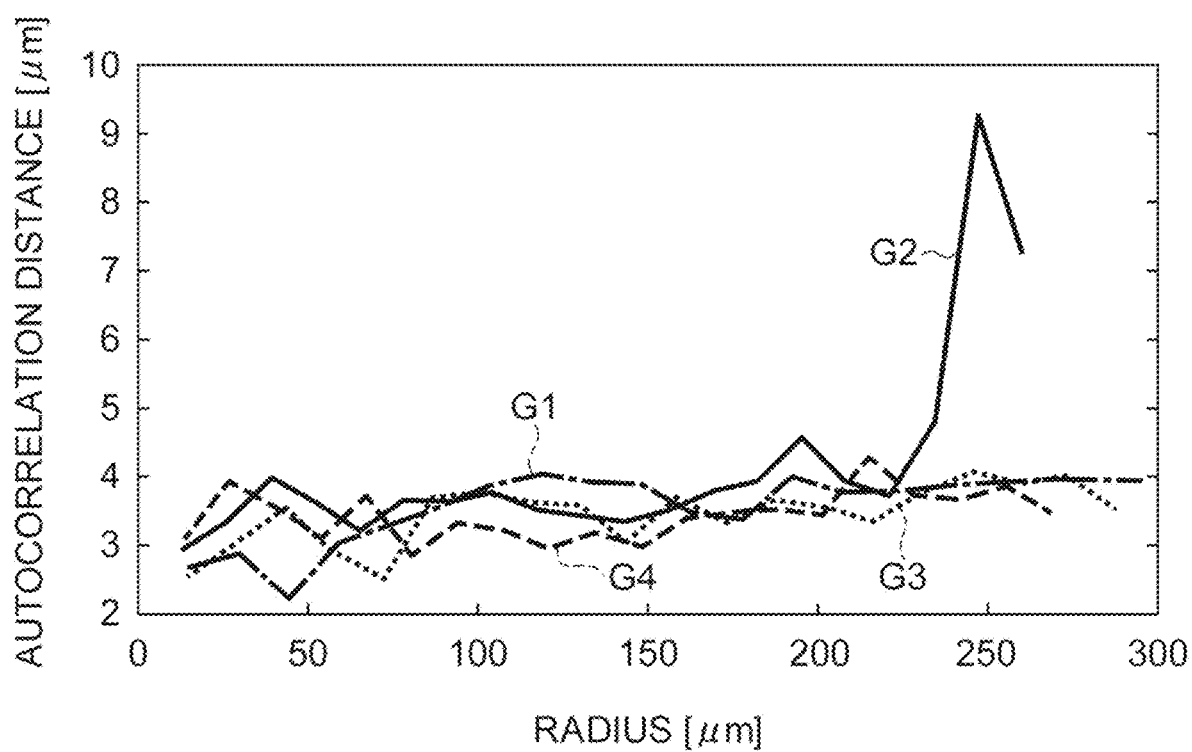
FIG. 7 is a graph illustrating a correlation between an autocorrelation distance and a radius of a sampling circle.

(a) in FIG. 5, (b) in FIG. 5, (a) in FIG. 6, and (b) in FIG. 6 illustrate images indicating a state where a plurality of sampling circles are set for each of image data D1 to D4 of different cell masses CM1 to CM4 (four sampling circles C1 to C4 are representatively shown in the figure). Further, FIG. 7 is a graph illustrating the correlation between the autocorrelation distance and the radius of the sampling circle obtained from each of these cell masses CM1 to CM4. In FIG. 7, graphs G1 to G4 show the correlations in the cell masses CM1 to CM4, respectively.

In addition, in this example, the cell mass CM was crushed to a thickness of 100 μm using a hemocytometer as the holding unit 5. Further, in order to quantitatively evaluate the cell number density, calibration was performed using the hemocytometer so as to have a uniform height. The cell masses CM1 to CM4 used were those on the 4th day after passage, and data analysis was carried out by selecting those having a radius of about 200 μm after height calibration. From the results illustrated in FIG. 7, it is understood that these cell masses CM1 to CM4 have a substantially constant cell number density in the radial direction, and are in an undifferentiated state. In addition, the fact that the autocorrelation distance at around a radius of 250 μm of the graph G2 is large is due to the influence of dust appearing in the image data D2. In this way, according to the evaluation method of the present embodiment, even when dust or the like different from cells is included in the image data, the state of the cell mass can be suitably evaluated.

Further, as in the evaluation method of the present embodiment, a plurality of sampling circles C1 to C4 having radii different from each other centered on the common reference point A may be set for one cell mass CM, a plurality of parameters for the state of the cell mass CM may be determined respectively based on the image data included in the regions on these sampling circles C1 to C4, and the cell mass CM may be evaluated based on the comparison of the plurality of parameters. In this case, the state of stem cells on the sampling circles C1 to C4 can be relatively evaluated. Therefore, the tendency of the state change of the cell mass CM can be easily found.

Further, as in the state analysis apparatus 1A of the present embodiment, the analysis unit 17 may set a plurality of sampling circles C1 to C4 having radii different from each other centered on the common reference point A for one cell mass CM, and may determine a plurality of parameters based on the image data included in the regions on the plurality of sampling circles C1 to C4. Thus, it is possible to provide the state analysis apparatus 1A capable of suitably performing the above evaluation method.

Further, when observing the cell mass CM with a microscope, the size of the cell mass CM is a problem. That is, unlike individual cells, the diameter of the cell mass CM is a relatively large value such as 50 to 400 μm. In a general optical microscope used for cell observation, visible light is often used as the illumination light source, and in this case, causing influence of light scattering inside the cell mass CM significantly. For such a problem, in the present embodiment, the light for irradiating the cell mass CM is infrared light.

Figure 8:
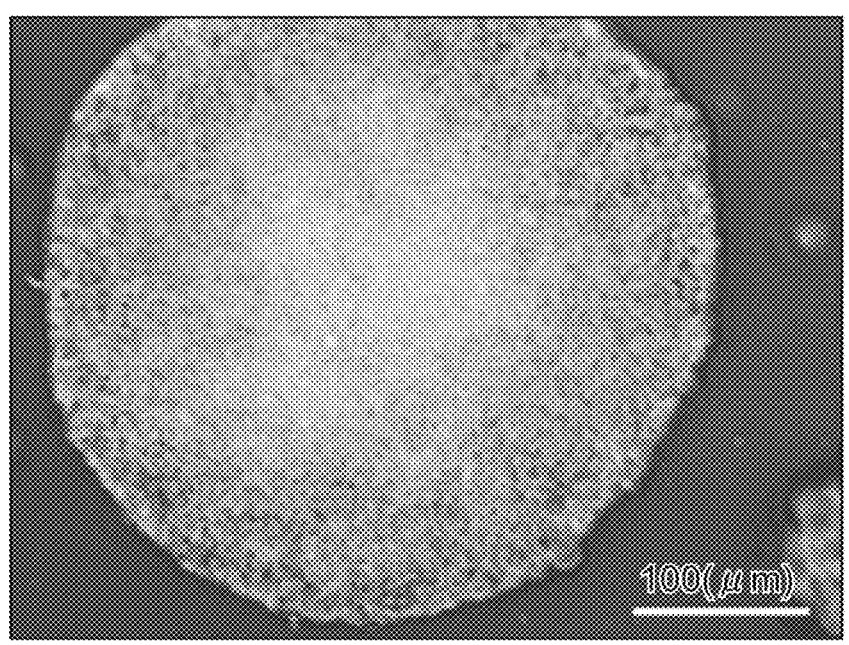
FIG. 8 includes (a) image data obtained by irradiating a cell mass with visible light and imaging transmitted light, and (b) image data obtained by irradiating a cell mass with infrared light and imaging transmitted light.
Figure 8:
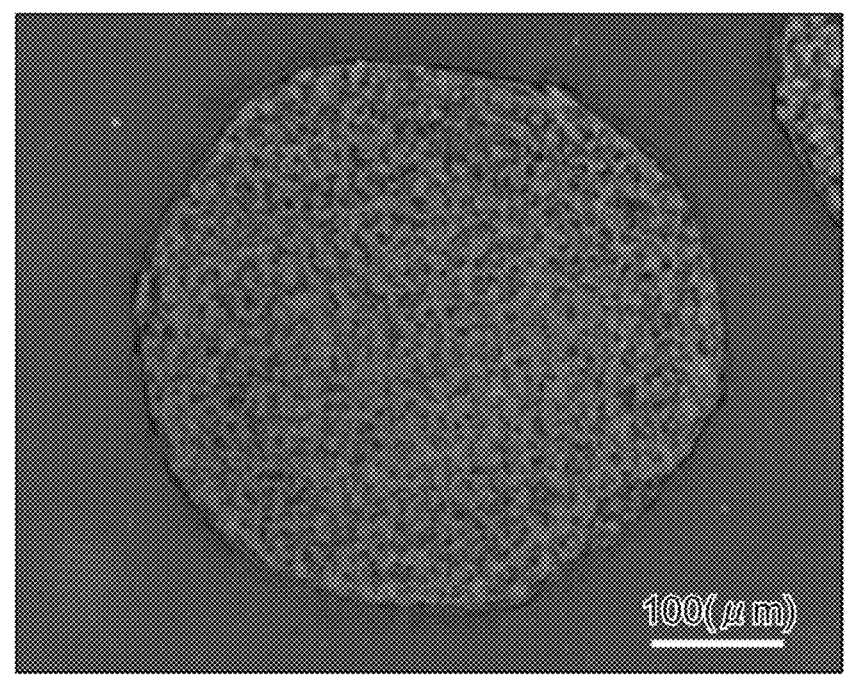

(a) in FIG. 8 illustrates image data obtained by irradiating the cell mass CM with visible light (wavelength 660 nm) and imaging the transmitted light. (b) in FIG. 8 illustrates image data obtained by irradiating the cell mass CM with infrared light (wavelength 1450 nm) and imaging the transmitted light. In these figures, the light intensity of each pixel is indicated by gray scale. These cell masses CM are cultured in the same dish, and the diameter of each cell mass CM is about 400 μm.

When the cell mass CM is irradiated with visible light, as illustrated in (a) in FIG. 8, since the light scattering inside the cell mass CM is strong, the optical density value in the vicinity of the center of the cell mass CM is high, so that it is difficult to perform imaging clearly. On the other hand, when the cell mass CM is irradiated with infrared light, as illustrated in (b) in FIG. 8, since the light scattering inside the cell mass CM is weak, the optical density value near the center of the cell mass CM does not increase even when the thickness of the cell mass CM in the light transmission direction is large (for example, 100 μm or more), so that it is possible to clearly image the whole region including the vicinity of the center.

Further, as in the present embodiment, the cell mass CM crushed into a thin layer shape may be irradiated with light from the thickness direction. In this case, the thickness of the cell mass CM in the light transmission direction can be thinner than the diameter, and the whole region including the vicinity of the center of the cell mass CM can be clearly imaged. Further, since the thicknesses of the cell mass CM in a plurality of sampling circles can be made equal to each other, comparison of the parameters is easy.

FIRST EXAMPLE

The first example of the above embodiment will be described in detail.

(1) Preparation of observation sample

First, the cultured cell mass CM is taken out from the culture dish using a pipette. At this time, the cell mass CM is carefully taken out so as not to be crushed. When the culture solution B is taken in vigorously, the cell mass CM will be damaged, so that the culture solution B is taken in gently. Next, the cell mass CM is placed together with the culture solution B in the vicinity of the center of the hemocytometer (holding unit 5) prepared in advance. Further, a cover glass (lid portion 5c) is placed on the cell mass CM, and the cell mass CM is crushed to make the thickness of the cell mass CM uniform (100 μm). Subsequently, the hemocytometer is set on the sample stage.

(2) Observation

First, the computer 21 including the analysis unit 17 and the evaluation unit 19 is activated. Next, the infrared light source (light source 3) is turned on. Before or after this, the infrared camera (imaging unit 15) is activated. Further, the sample stage or the objective lens 7 is moved in the optical axis direction to adjust the focal position. The position of the hemocytometer in the direction intersecting the optical axis direction is adjusted so that the cell mass CM is in the field of view. The infrared light that has transmitted through the cell mass CM is imaged by the infrared camera (imaging unit 15) to acquire image data D.

Figure 9:
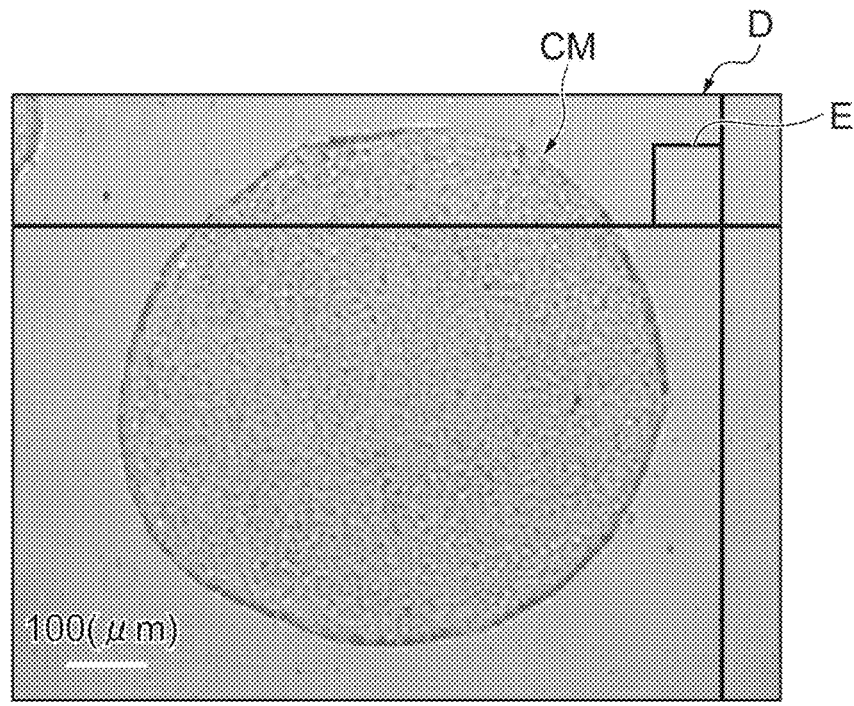
FIG. 9 includes (a) a diagram illustrating image data acquired in a first example, and (b) a diagram illustrating a state in which a plurality of points inside a contour of a cell mass are set along a circumferential direction.
Figure 9:
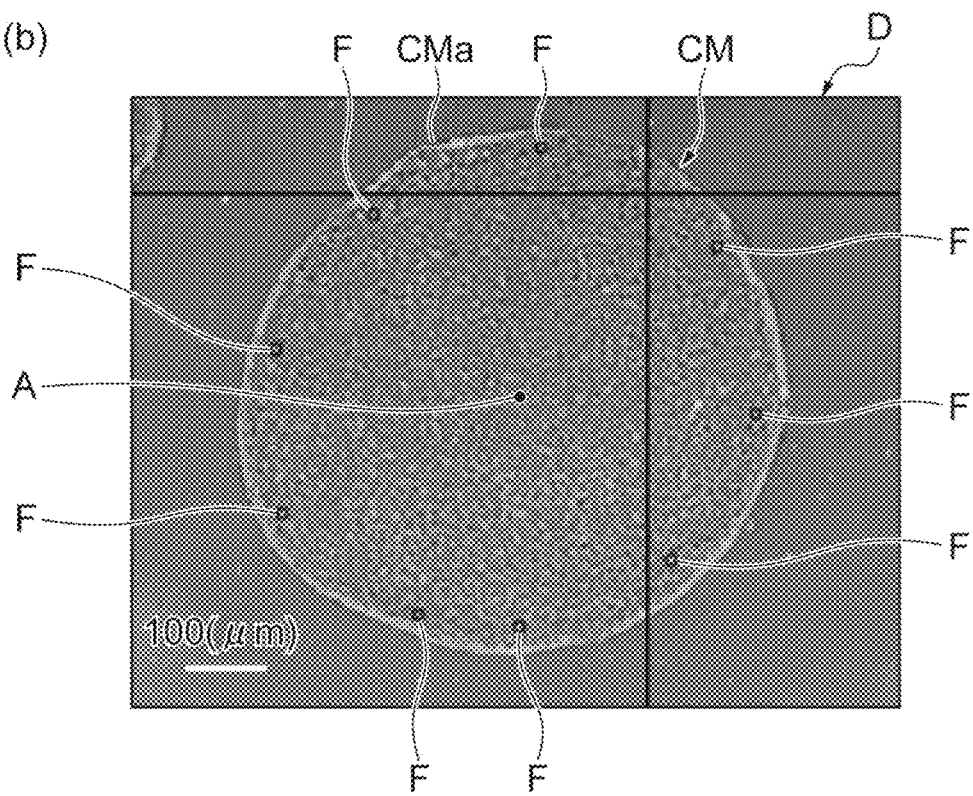

(3) Analysis and evaluation (a) in FIG. 9 illustrates the acquired image data D. First, normalization of pixel values is performed on the image data D. That is, a background region (region where there is no cell mass CM) E is selected, and the average value of the background intensity (background) is calculated. At this time, for example, a quadrangular region E is selected at two corners located diagonally among the four corners where there is no cell mass CM. Next, normalization of each pixel value of a plurality of pixels included in the image data D is performed using the following formula.

(Normalized pixel value)=$\log_{10}${(pixel value)/(average value of background)}

Figure 10:
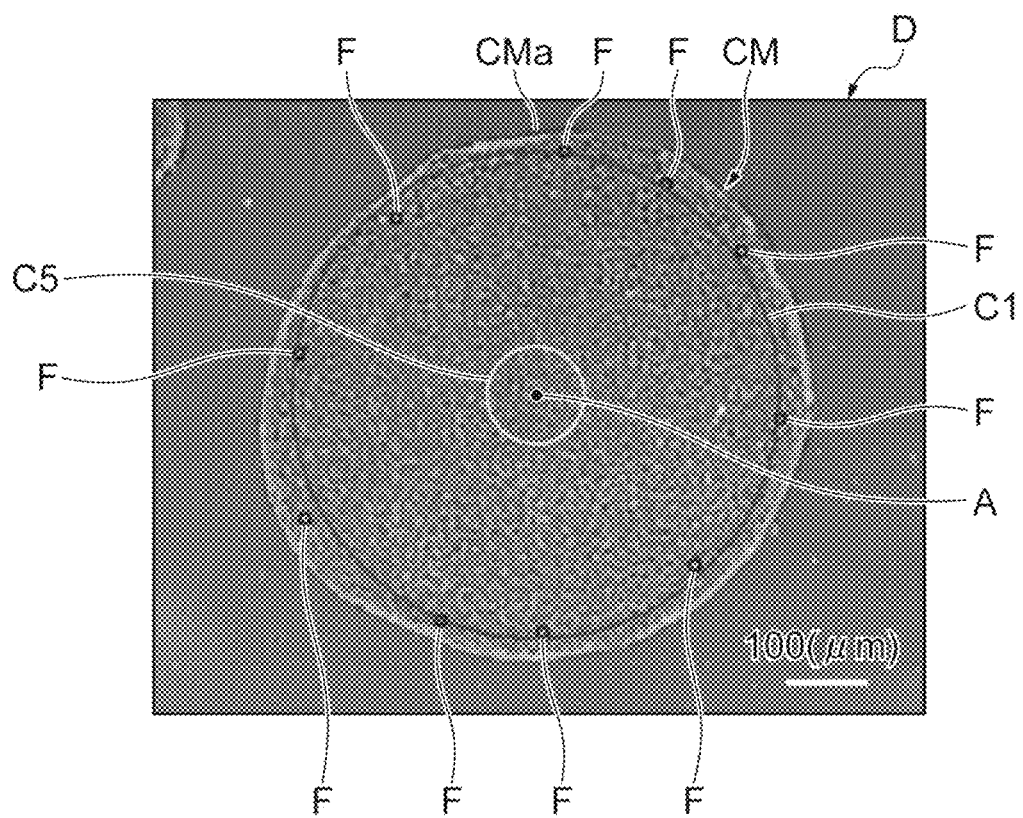
FIG. 10 is a diagram illustrating a state in which a sampling circle is set.

Subsequently, the cell mass CM to be evaluated is selected from among a plurality of cell masses CM included in the image data D. Further, as illustrated in (b) in FIG. 9, a plurality of points F (10 points in this example) inside of the contour CMa of the cell mass CM is set along the circumferential direction. Subsequently, the coordinate of the reference point A at which distances from the plurality of points F are substantially equal is calculated using the least square center method, and this reference point A is set as the central point of the cell mass CM. Thereafter, as illustrated in FIG. 10, a sampling circle C1 whose radius is the average distance between the plurality of points F and the reference point A is set. A sampling circle C5 which is concentric with the sampling circle C1 and whose radius is 0.2 times the sampling circle C1 is further set.

Figure 11:
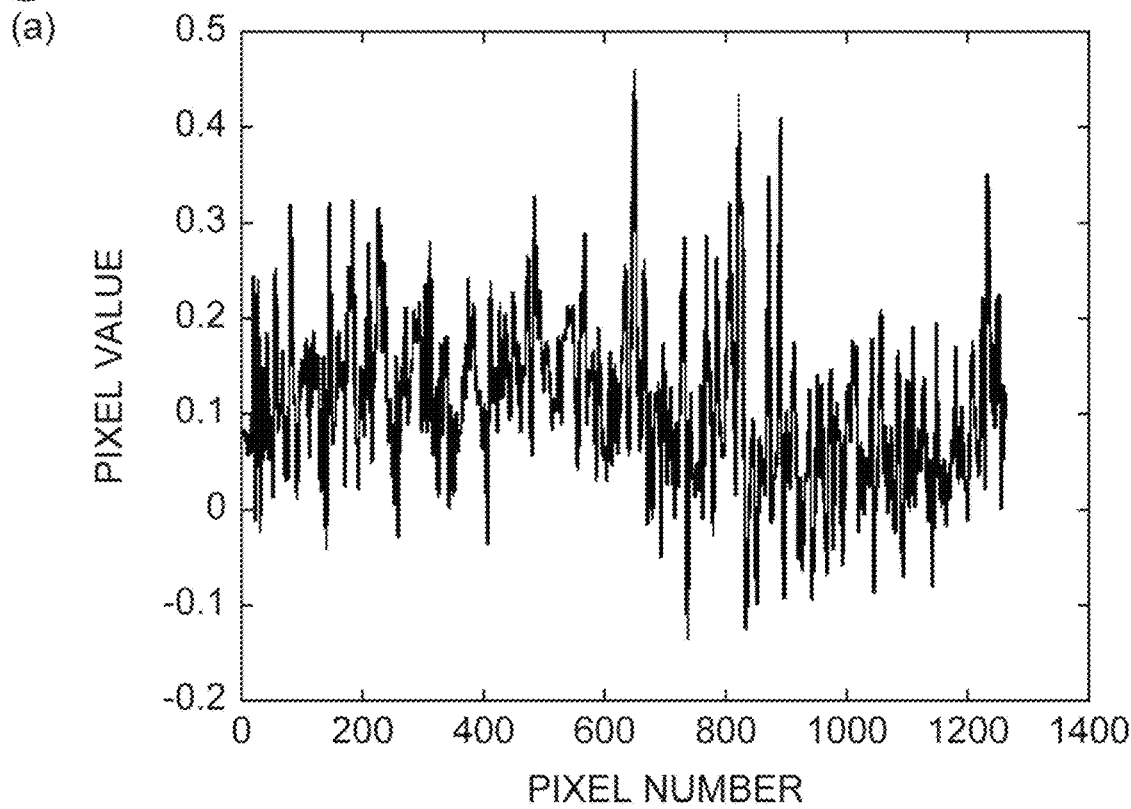
FIG. 11 includes (a), (b) graphs illustrating a pixel value sequence on a sampling circle.
Figure 11:
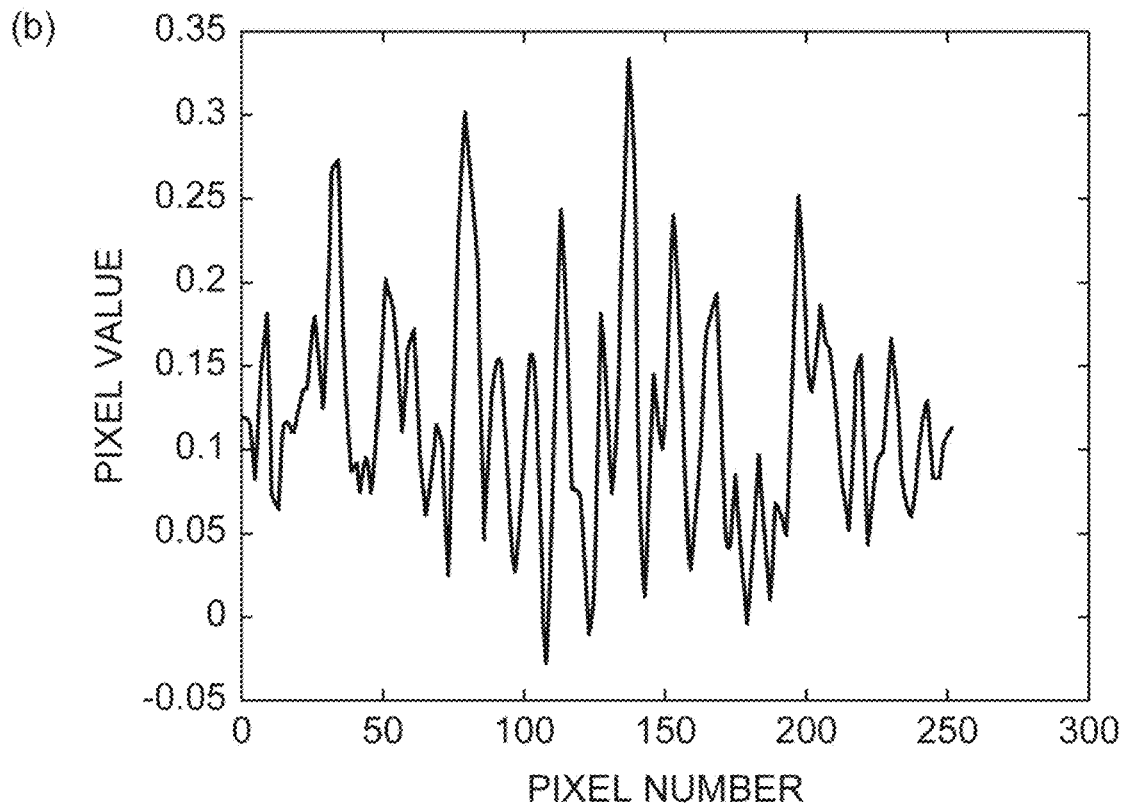

The pixel values on the sampling circles C1 and C5 thus set are extracted. (a) in FIG. 11 and (b) in FIG. 11 are graphs illustrating a pixel value sequence on the sampling circles C1 and C5, respectively, where the vertical axis represents the pixel value (intensity) and the horizontal axis represents the pixel number. Further, the autocorrelation function $R_{OD}$($\Delta$r') is calculated for the extracted sequence of pixel values using the above Formula (1).

Figure 12:
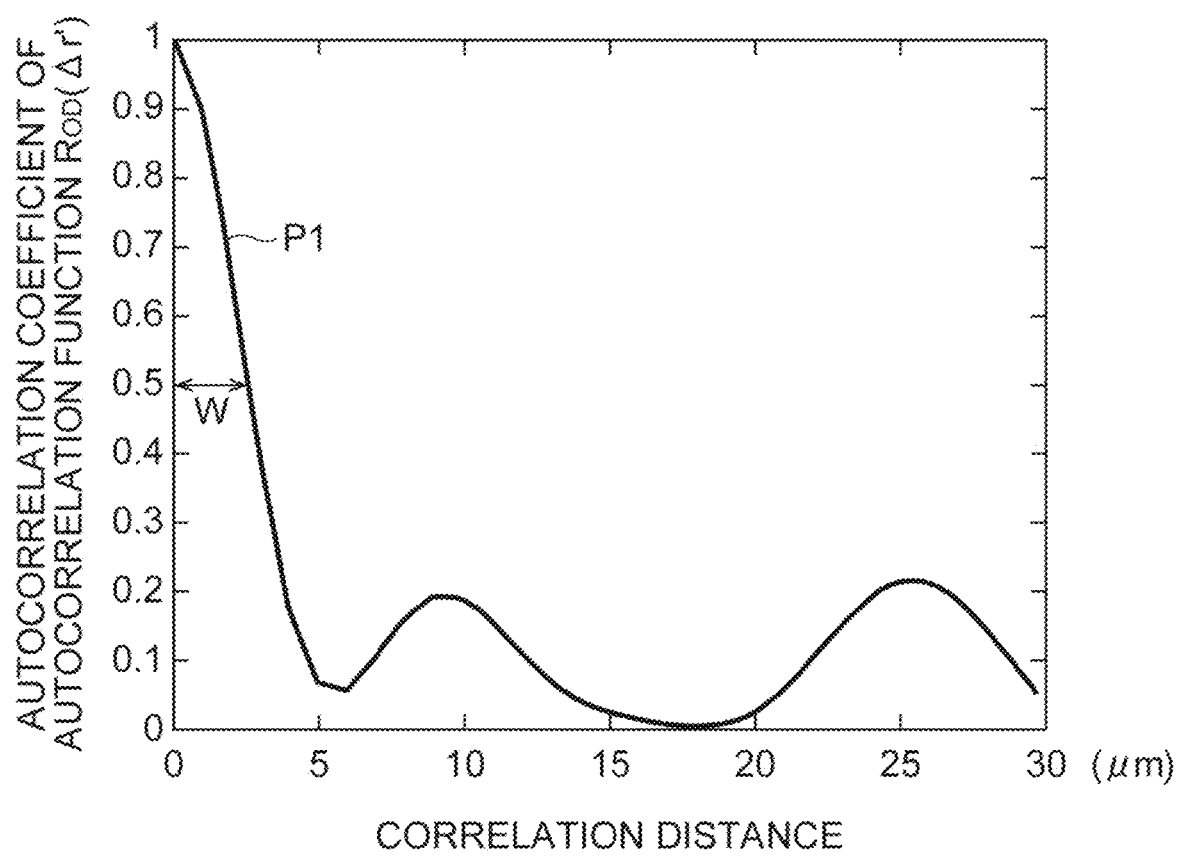
FIG. 12 is a graph illustrating an autocorrelation function.

FIG. 12 is a graph illustrating the autocorrelation function $R_{OD}$($\Delta$r') for the sampling circle C1, where the vertical axis represents the autocorrelation coefficient of the autocorrelation function $R_{OD}$($\Delta$r'), and the horizontal axis represents the correlation distance. The width W of the first waveform P1 of this autocorrelation function is $R_{OD}$($\Delta$r') calculated as the autocorrelation distance for the sampling circle C1. In addition, the width W is a width at a value of 1/N of the maximum value of the autocorrelation coefficient (N>1), and for example, in the case of N=2, the width W is a width at half value of the maximum value. Further, to reduce the influence of noise, the autocorrelation distance is calculated for each of a sampling circle having a radius smaller by one pixel than the radius of the sampling circle C1 and a sampling circle having a radius larger by one pixel, and the average value of the calculated autocorrelation distances is taken as the average autocorrelation distance of the sampling circle C1. The average autocorrelation distance is similarly determined for the sampling circle C5.

The respective average autocorrelation distances obtained for the sampling circles C1 and C5 are compared with each other to evaluate the state of the cell mass CM. In this example, the average autocorrelation distance of the sampling circle C1 is 3.9 μm, and the average autocorrelation distance of the sampling circle C5 is 3.5 μm. Therefore, it is evaluated that the cell number density is almost uniform in the radial direction of the cell mass CM, and the degree of differentiation is almost constant.

(First Modification)

In the above embodiment, in the imaging step S1, (the imaging unit 15) generates the image data D including one cell mass CM, and sets a plurality of sampling circles C1 to C4 for the one cell mass CM.

Figure 13:
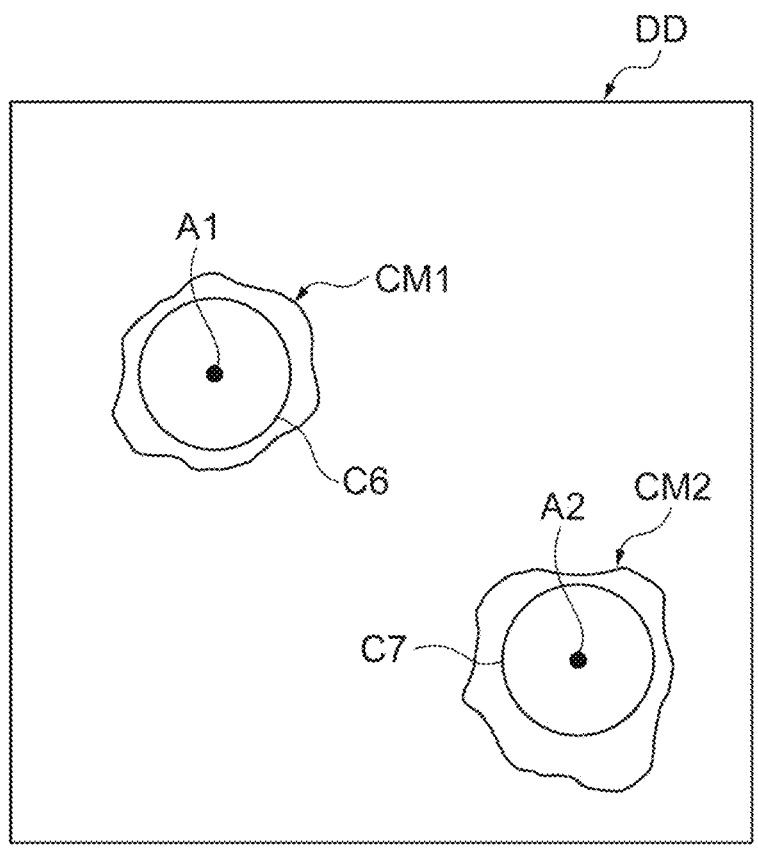
FIG. 13 is a diagram illustrating image data including a first cell mass and a second cell mass acquired in a first modification.

In the present modification, as illustrated in FIG. 13, in the imaging step S1, (the imaging unit 15) acquires image data DD including a cell mass CM1 (first cell mass) and a cell mass CM2 (second cell mass) different from the cell mass CM1. Further, in the analysis step S2, (the analysis unit 17) sets reference points A1 and A2 and sampling circles C6 and C7 individually for the cell masses CM1 and CM2 included in the image data DD, determines a first parameter based on image data on the sampling circle C6 of the cell mass CM1, and determines a second parameter based on image data on the sampling circle C7 of the cell mass CM2. In addition, the first parameter and the second parameter are the same as those in the above embodiment (for example, the cell number density or the width of the first waveform of the autocorrelation function). Further, in the evaluation step S3 (by the evaluation unit 19), at least one of the states of the cell masses CM1 and CM2 (for example, the degree of differentiation) is evaluated based on the comparison of the first parameter and the second parameter.

In this way, the first parameter for the cell mass CM1 and the second parameter for the cell mass CM2 are determined, and by comparing these parameters, the state of stem cells in the cell mass CM1 and the state of stem cells in the cell mass CM2 can be relatively evaluated. Therefore, for example, when the cell masses CM1 and CM2 are cultured in the same container, it is possible to easily evaluate the degree of stability of the state of the plurality of cell masses simultaneously cultured in the container. Further, when the state analysis apparatus includes the imaging unit 15 and the analysis unit 17 of the present modification, the state analysis apparatus capable of suitably performing the evaluation method of the present modification can be provided. In addition, in the present modification, a plurality of sampling circles may be set for each of the cell masses CM1 and CM2, and a plurality of parameters may be acquired for each of the cell masses CM1 and CM2. Further, although the parameters for two cell masses are compared in this example, parameters for three or more cell masses may be acquired and compared with each other.

(Second Modification)

Figure 14:
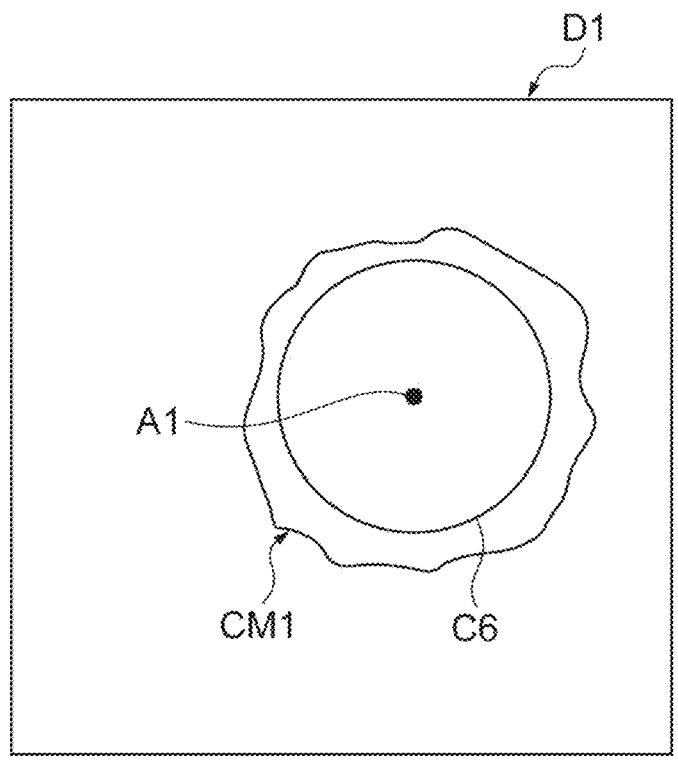
FIG. 14 includes (a) a diagram illustrating first image data including a first cell mass, and (b) a diagram illustrating second image data including a second cell mass.
Figure 14:
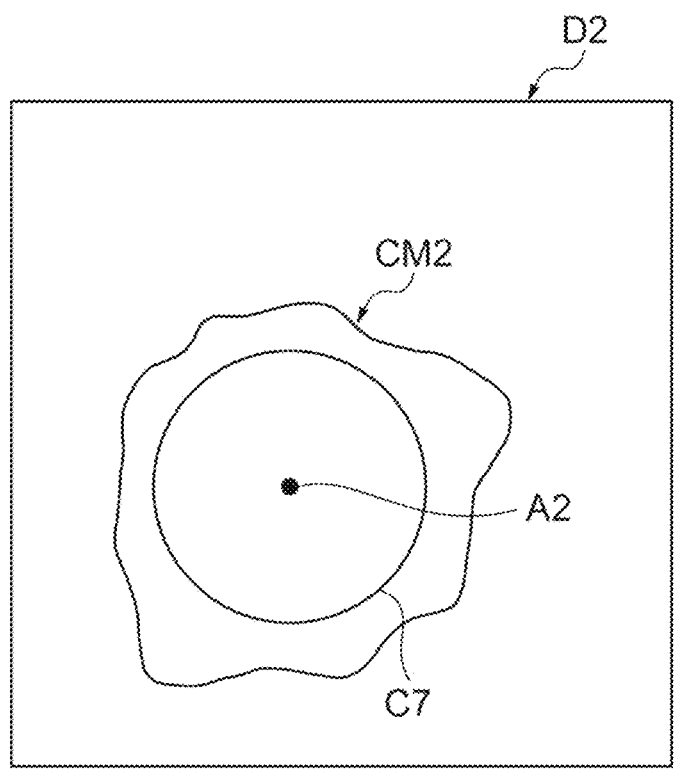

In the present modification, as illustrated in (a) in FIG. 14 and (b) in FIG. 14, in the imaging step S1, (the imaging unit 15) acquires image data D1 (first image data) including a cell mass CM1 (first cell mass) and image data D2 (second image data) including a cell mass CM2 (second cell mass) different from the cell mass CM1. Further, in the analysis step S2, (the analysis unit 17) sets a reference point A1 and a sampling circle C6 for the cell mass CM1 included in the image data D1, and sets a reference point A2 and a sampling circle C7 for the cell mass CM2 included in the image data D2. Thereafter, in the analysis step S2, (the analysis unit 17) determines a first parameter based on image data on the sampling circle C6 of the cell mass CM1 and determines a second parameter based on image data on the sampling circle C7 of the cell mass CM2. In addition, the first parameter and the second parameter are the same as those in the above embodiment (for example, the cell number density or the width of the first waveform of the autocorrelation function). Further, in the evaluation step S3 (by the evaluation unit 19), at least one of the states of the cell masses CM1 and CM2 (for example, the degree of differentiation) is evaluated based on the comparison of the first parameter and the second parameter.

In this way, the first parameter for the cell mass CM1 and the second parameter for the cell mass CM2 are determined, and by comparing these parameters, the state of stem cells in the cell mass CM1 and the state of stem cells in the cell mass CM2 can be relatively evaluated. Therefore, for example, when the cell masses CM1 and CM2 are cultured in the same container, it is possible to easily evaluate the degree of stability of the state of the plurality of cell masses simultaneously cultured in the container. In addition, in the present modification, a plurality of sampling circles may be set for each of the cell masses CM1 and CM2, and a plurality of parameters may be acquired for each of the cell masses CM1 and CM2. Further, although the parameters for two cell masses are compared in this example, parameters for three or more cell masses may be acquired and compared with each other.

(Third Modification)

Figure 15:
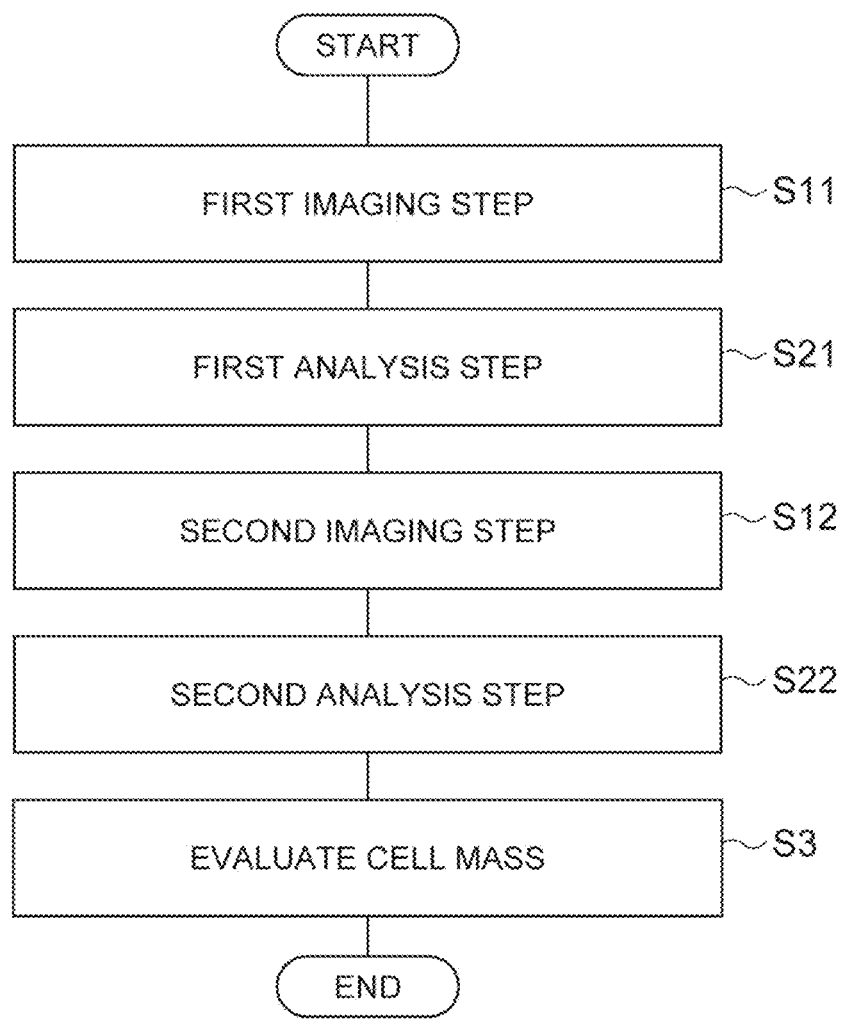
FIG. 15 is a flowchart illustrating an evaluation method according to a third modification.

A flowchart of the evaluation method according to the present modification is illustrated in FIG. 15. The evaluation method of the present modification includes a first imaging step S11, a first analysis step S21, a second imaging step S12, and a second analysis step S22. In addition, the details of the first imaging step S11 and the second imaging step S12 are the same as those in the imaging step S1 of the above embodiment, and the details of the first analysis step S21 and the second analysis step S22 are the same as those in the analysis step S2 of the above embodiment.

In the first imaging step S11, the image data D1 (see (a) in FIG. 14) including the cell mass CM1 is acquired. In the first analysis step S21, the reference point A1 and the sampling circle C6 are set for the cell mass CM1 included in the image data D1, and the first parameter is determined based on the image data on the sampling circle C6 of the cell mass CM1. In the second imaging step S12, the image data D2 (see (b) in FIG. 14) including the cell mass CM2 is acquired. In the second analysis step S22, the reference point A2 and the sampling circle C7 are set for the cell mass CM2 included in the image data D2, and the second parameter is determined based on the image data on the sampling circle C7 of the cell mass CM2. In addition, the first parameter and the second parameter are the same as those in the above embodiment (for example, the cell number density or the width of the first waveform of the autocorrelation function). Further, in the evaluation step S3, at least one of the states of the cell masses CM1 and CM2 (for example, the degree of differentiation) is evaluated based on the comparison of the first parameter and the second parameter.

According to such a method, the same effect as that of the above second modification can be obtained. In addition, in the present modification, a plurality of sampling circles may be set for each of the cell masses CM1 and CM2, and a plurality of parameters may be acquired for each of the cell masses CM1 and CM2. Further, although the parameters for two cell masses are compared in this example, parameters for three or more cell masses may be acquired and compared with each other.

(Fourth Modification)

In the present modification, at least two pieces of image data are acquired at different timings for a certain non-crushed cell mass, and the parameter is determined based on the image data. Specifically, in the imaging step, (the imaging unit 15) acquires, as illustrated in (a) in FIG. 16, image data D3 (first image data) including the cell mass CM at a first timing. Next, in the imaging step, (the imaging unit 15) acquires, as illustrated in (b) in FIG. 16, image data D4 (second image data) including the same cell mass CM at a second timing after the first timing. The time difference between the first timing and the second timing is, for example, several days.

Further, in the analysis step S2, (the analysis unit 17) sets a reference point A3 and a sampling circle C8 for the cell mass CM included in the image data D3, and sets a reference point A4 and a sampling circle C9 for the cell mass CM included in the image data D4. Thereafter, in the analysis step S2, (the analysis unit 17) determines a first parameter based on image data on the sampling circle C8, and determines a second parameter based on image data on the sampling circle C9. In addition, the first parameter and the second parameter are the same as those in the above embodiment (for example, the cell number density or the width of the first waveform of the autocorrelation function). Further, in the evaluation step S3 (by the evaluation unit 19), the state of the cell mass CM (for example, the degree of differentiation) is evaluated based on the comparison of the first parameter and the second parameter.

In this way, by comparing the plurality of parameters obtained at different timings for the same cell mass CM, it is possible to easily find the change with time of the state (or the fact that the state remains unchanged) of the cells constituting the cell mass CM. In addition, in the present modification, a plurality of sampling circles may be set for each timing, and a plurality of parameters may be acquired for each timing. Further, although the parameters are acquired at two timings in this example, the parameters may be acquired at three or more timings and these may be compared with each other.

(Fifth Modification)

Figure 17:
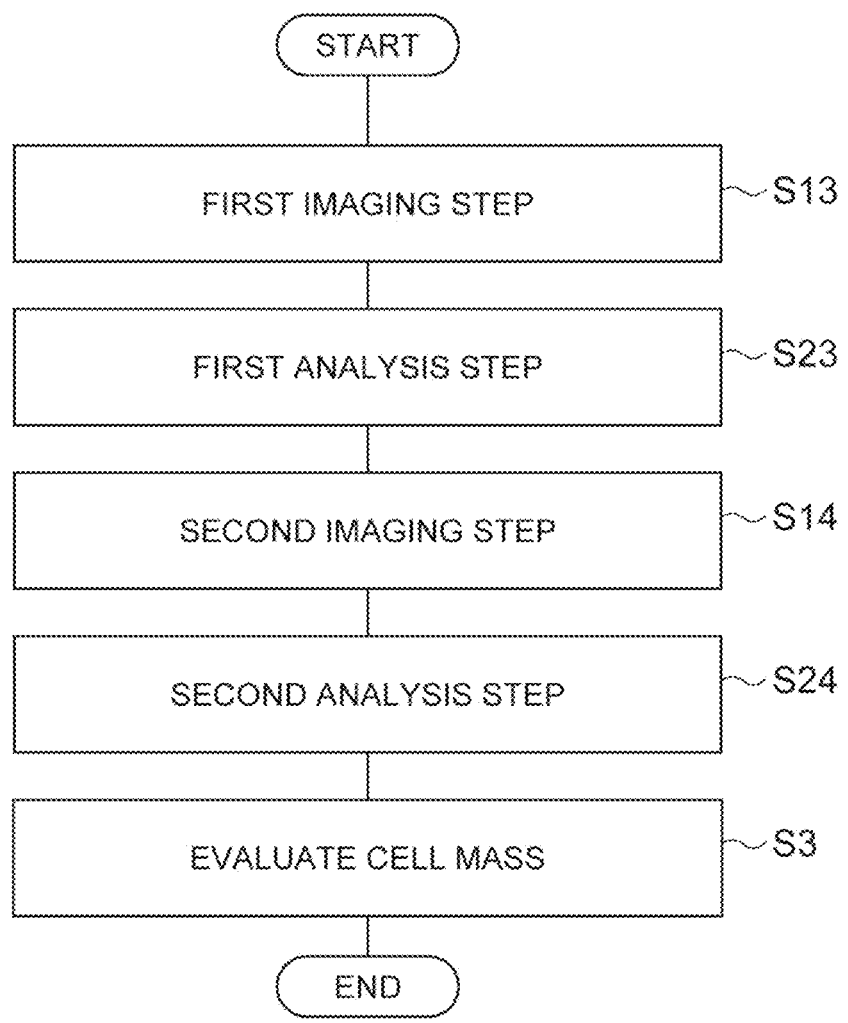
FIG. 17 is a flowchart illustrating an evaluation method according to a fifth modification.

A flowchart of the evaluation method according to the present modification is illustrated in FIG. 17. The evaluation method of the present modification includes a first imaging step S13, a first analysis step S23, a second imaging step S14, and a second analysis step S24. In addition, the details of the first imaging step S13 and the second imaging step S14 are the same as those in the imaging step S1 of the above embodiment, and the details of the first analysis step S23 and the second analysis step S24 are the same as those in the analysis step S2 of the above embodiment.

Figure 16:
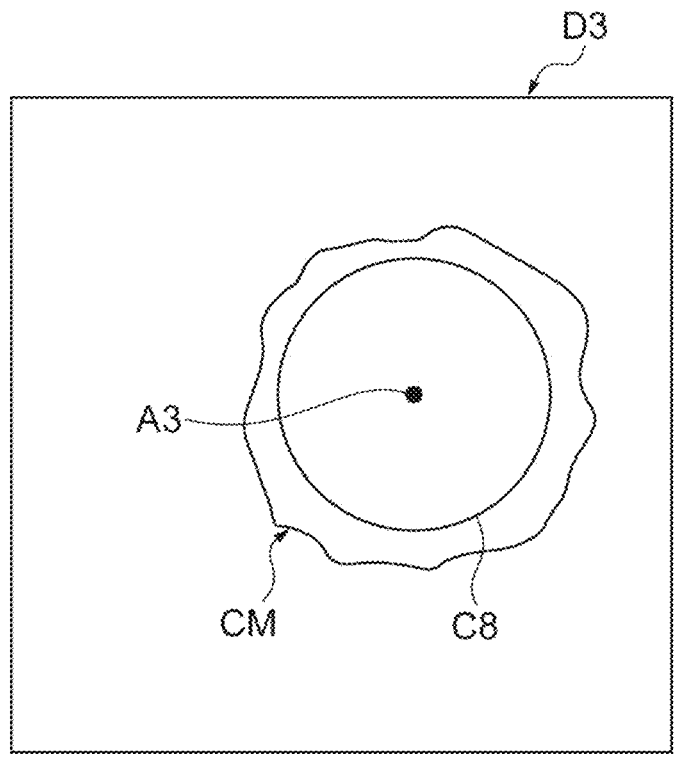
FIG. 16 includes (a) a diagram illustrating first image data including a cell mass acquired at a first timing, and (b) a diagram illustrating second image data including the same cell mass acquired at a second timing.
Figure 16:
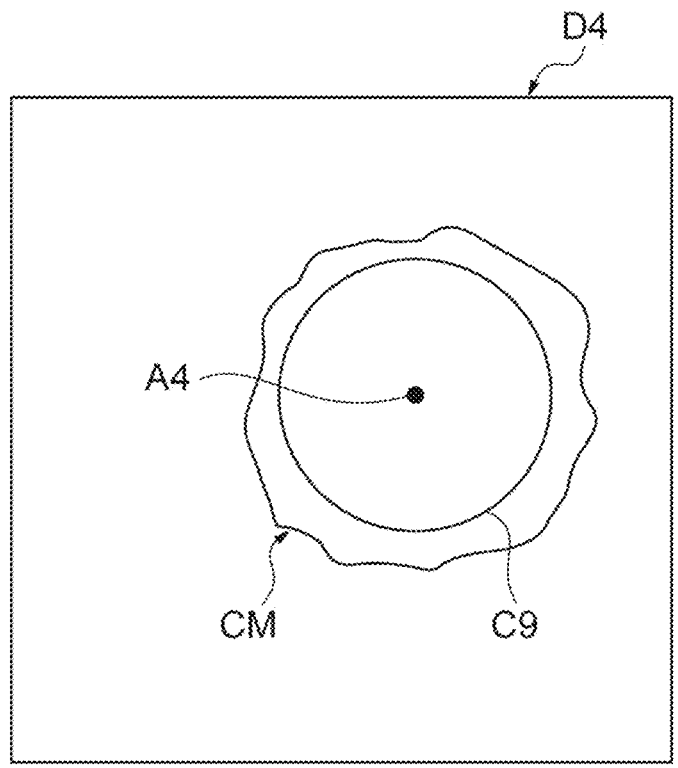

In the first imaging step S13, the image data D3 (see (a) in FIG. 16) including the cell mass CM is acquired at the first timing. In the first analysis step S23, the reference point A3 and the sampling circle C8 are set for the cell mass CM included in the image data D3, and the first parameter is determined based on the image data on the sampling circle C8 of the cell mass CM. In the second imaging step S14, the image data D4 (see (b) in FIG. 16) including the same cell mass CM is acquired at the second timing after the first timing. In the second analysis step S24, the reference point A4 and the sampling circle C9 are set for the cell mass CM included in the image data D4, and the second parameter is determined based on the image data on the sampling circle C9 of the cell mass CM. In addition, the first parameter and the second parameter are the same as those in the above embodiment (for example, the cell number density or the width of the first waveform of the autocorrelation function). Further, in the evaluation step S3, the state of the cell mass CM (for example, the degree of differentiation) is evaluated based on the comparison of the first parameter and the second parameter.

According to such a method, the same effect as that of the above fourth modification can be obtained. In addition, in the present modification, a plurality of sampling circles may be set for each timing, and a plurality of parameters may be acquired for each timing. Further, although the parameters are acquired at two timings in this example, the parameters may be acquired at three or more timings and these may be compared with each other.

SECOND EXAMPLE

Figure 18:
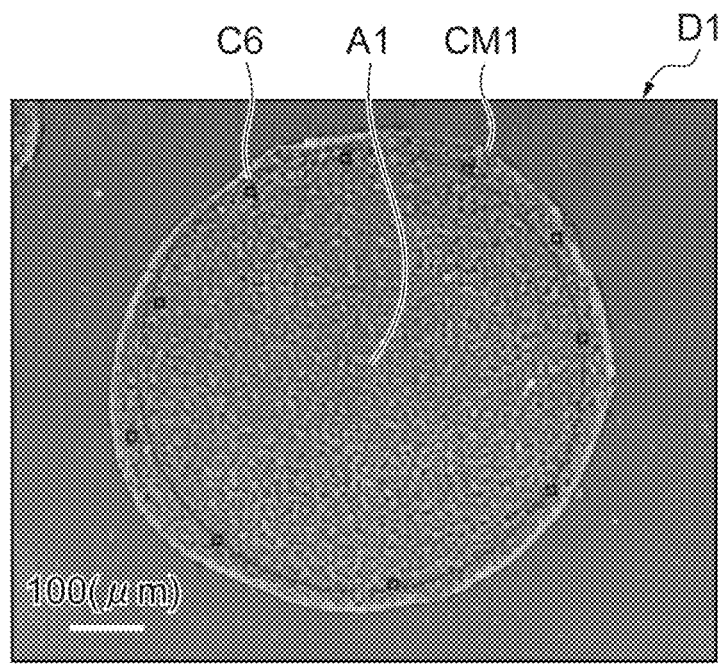
FIG. 18 includes (a), (b) diagrams illustrating image data after normalization obtained in a second example.
Figure 18:
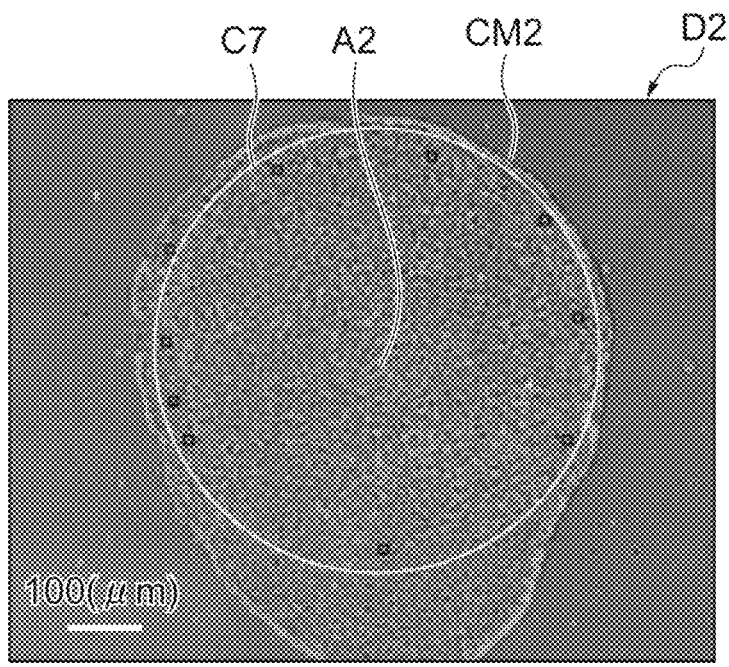

The example will be described in which two cell masses cultured for 4 days in the same culture dish were analyzed, and were compared. First, image data D1 including a certain cell mass CM1 was acquired in the same manner as the method shown in the first example. Next, image data D2 including another cell mass CM2 was acquired in the same manner as the method shown in the first example. The magnification of the objective lens 7 used at this time was 10 times, and the resolution of the infrared camera was 2.97 (μm/pixel). Further, the pixel values were normalized for the image data D1 and D2. (a) in FIG. 18 and (b) in FIG. 18 illustrate the image data D1 and D2 after normalization, respectively.

Subsequently, reference points A1 and A2 of the cell masses CM1 and CM2 were calculated in the same manner as the method shown in the first example. Thereafter, a sampling circle C6 centered on the reference point A1 and a sampling circle C7 centered on the reference point A2 were set. At this time, the radius of the sampling circle C6 was determined by the method shown in the first example, and the radius of the sampling circle C7 was made to coincide with the radius of the sampling circle C6. Subsequently, pixel values on the sampling circle C6 were extracted. The autocorrelation function $R_{OD}(\Delta r')$ was calculated for the extracted sequence of pixel values using the above Formula (1), and the autocorrelation distance for the sampling circle C6 was determined. Further, to reduce the influence of noise, the autocorrelation distance was calculated for each of the sampling circle having a radius smaller by one pixel than the radius of the sampling circle C6 and the sampling circle having a radius larger by one pixel, and the average value of the autocorrelation distances was calculated as the average autocorrelation distance. The average autocorrelation distance was similarly calculated for the sampling circle C7.

The respective average autocorrelation distances obtained for the sampling circles C6 and C7 were compared with each other to relatively evaluate the states of the cell masses CM1 and CM2. In this example, the average autocorrelation distance of the sampling circle C6 was 3.8 μm, and the average autocorrelation distance of the sampling circle C7 was 3.7 μm. Therefore, it was evaluated that the cell number densities of the cell masses CM1 and CM2 were substantially equal, and the degrees of differentiation were substantially the same.

THIRD EXAMPLE

Figure 19:
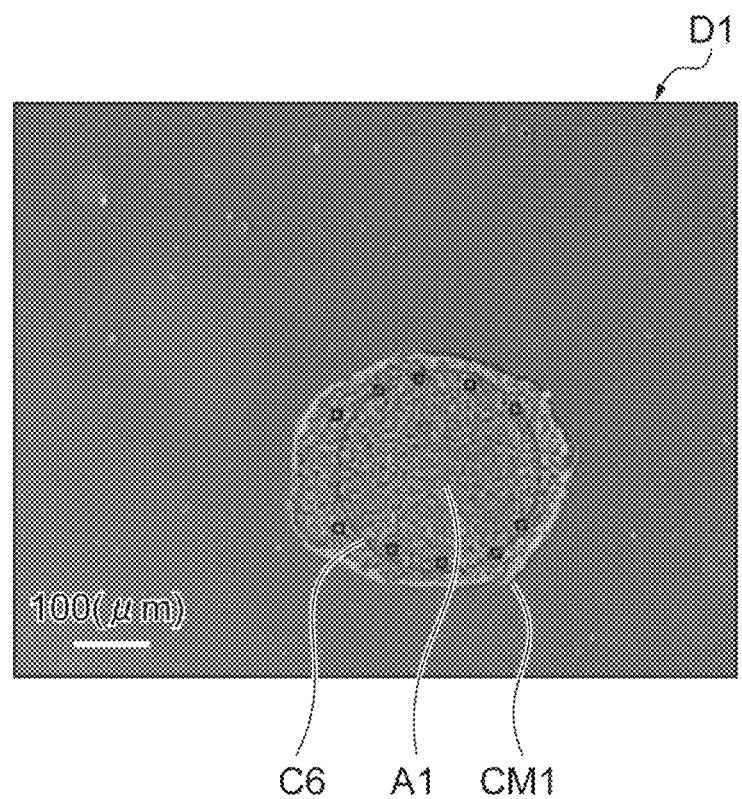
FIG. 19 includes (a), (b) diagrams illustrating image data after normalization obtained in a third example.
Figure 19:

The example will be described in which two cell masses of a cell mass CM1 (culture days: 4 days) and a cell mass CM2 (culture days: 6 days) which are cultured in different culture dishes and different in culture days were analyzed and compared. In addition, the acquisition and normalization of the image data D1 and D2 for the cell masses CM1 and CM2, the calculation of the reference points A1 and A2, the setting of the sampling circles C6 and C7, and the calculation of the average autocorrelation distances were performed in the same manner as the second example described above. The magnification of the objective lens 7 used for the image data D1 was 10 times, and the resolution of the infrared camera was 2.97 (μm/pixel). The magnification of the objective lens 7 used for the image data D2 was 20 times, and the resolution of the infrared camera was 1.98 (μm/pixel). (a) in FIG. 19 and (b) in FIG. 19 illustrate the image data D1 and D2 after normalization, respectively. In this example, the average autocorrelation distance of the sampling circle C6 was 3.5 μm, and the average autocorrelation distance of the sampling circle C7 was 2.7 μm. Therefore, no significant difference between the cell number densities of the cell masses CM1 and CM2 was found, and the degrees of differentiation were evaluated to be substantially the same.

The cell mass evaluation method and the cell mass state analysis apparatus are not limited to the embodiments described above, and various modifications can be made. For example, the embodiments and the modifications described above may be combined with each other depending on the required purpose and effect. Further, in the above embodiments and modifications, the cell number density is exemplified as a parameter for the state of the cell mass, but the present invention is not limited to the above parameter, and various other values related to the state of cell mass can be used as a parameter.

Further, although the above embodiments and modifications show the example in which the degree of differentiation of the cell mass is evaluated based on the cell number density, the matter which can be evaluated based on the cell number density is not restricted to this. For example, Non-Patent Document 3 reports that addition of the reagent "TGF-β2" makes the cell shape elongated, compared to the control state. Thus, the reagent to be added may act on the cell morphology. Since the change of cell morphology is related to the cell number density, the cell number density can be used as an evaluation parameter even when screening is performed while, for example, evaluating the influence of a reagent on a cancer cell mass or the like.

Further, in the above embodiments and modifications, a plurality of parameters obtained from image data on a plurality of sampling circles are compared with each other, but the state of the cell mass may be evaluated based on a single parameter obtained from image data on a single sampling circle. For example, a single parameter may be used for evaluating the cell mass by defining an appropriate threshold value and determining whether the parameter exceeds the threshold value.

Further, in the above embodiments and modifications, the imaging unit 15 acquires two-dimensional image data. The imaging unit may acquire a three-dimensional image, and in this case, the parameter calculation can be performed without staining and non-invasively without crushing the cell mass based on the tomographic image. Further, in the above embodiments and modifications, although stem cells or cancer cells are described as cells constituting the cell mass CM, other types of cells may be used.

The cell mass evaluation method of the above embodiment is a method for evaluating a cell mass containing a plurality of aggregated cells, and is configured to include an imaging step of capturing an image of light obtained from the cell mass by irradiation with light to the cell mass, an analysis step of setting a reference point for the cell mass included in the image obtained by the imaging step, setting a sampling circle centered on the reference point, and determining a parameter for a state of the cell mass based on image data included in a region on the sampling circle, and an evaluation step of evaluating the cell mass based on the parameter.

Further, the cell mass state analysis apparatus of the above embodiment is an apparatus used for evaluating a cell mass containing a plurality of aggregated cells, and is configured to include a light source for outputting light for irradiating the cell mass, an imaging unit for capturing an image of light obtained from the cell mass by irradiation with the light, and an analysis unit for setting a reference point for the cell mass included in the image obtained by the imaging, setting a sampling circle centered on the reference point, and determining a parameter for a state of the cell mass based on image data included in a region on the sampling circle.

In the above evaluation method and the state analysis apparatus, the parameter may be a cell number density. For example, in stem cells such as iPS cells or ES cells, when the state of cells changes (for example, changes from undifferentiated state to differentiated state), individual cell morphology changes and a cell number density of the cell mass changes. Therefore, by determining the cell number density of the cell mass, it is possible to accurately evaluate the degree of differentiation of respective cells constituting the cell mass.

Further, in the above evaluation method and the state analysis apparatus, the parameter may be a width of a first waveform of an autocorrelation function of the image data along a circumferential direction of the sampling circle. According to the findings of the inventors, the width of the first waveform of the autocorrelation function is related to the cell number density on the sampling circle of the cell mass. Therefore, by determining the above width of the first waveform of the autocorrelation function, it is possible to estimate and compare the cell number density on the sampling circle of the cell mass, and the degree of differentiation of respective cells constituting the cell mass can be accurately evaluated.

In addition, in the above evaluation method, when the cell mass is constituted by stem cells, the evaluation step may include evaluating a degree of differentiation of the cell mass based on the parameter such as the cell number density and the width of the first waveform of the autocorrelation function. Further, the above state analysis apparatus may further include an evaluation unit for evaluating the cell mass based on the parameter such as the cell number density and the width of the first waveform of the autocorrelation function determined by the analysis unit. In addition, when the cell mass is constituted by stem cells, the evaluation unit may evaluate a degree of differentiation of the cell mass based on the parameter. In this case, the state of the cell mass can be evaluated, and in particular, the degree of differentiation of the cell mass constituted by the plurality of stem cells can be suitably evaluated.

Further, in the above evaluation method, the analysis step may include setting a plurality of sampling circles having radii different from each other centered on the common reference point for the cell mass, and determining a plurality of parameters for the state of the cell mass based on the image data included in the regions on the plurality of sampling circles, and the evaluation step may include evaluating the cell mass based on a comparison of the plurality of parameters. In this way, by determining the plurality of parameters from the image data on the plurality of sampling circles and comparing them, it is possible to relatively evaluate the state of cells on the plurality of sampling circles. Therefore, the tendency of the state change of the cell mass can be found easily.

Further, in the above state analysis apparatus, the analysis unit may set a plurality of sampling circles having radii different from each other centered on the common reference point for the cell mass, and may determine a plurality of parameters based on the image data included in the regions on the plurality of sampling circles. Thus, it is possible to provide the state analysis apparatus capable of suitably performing the above evaluation method.

Further, the imaging step of the above evaluation method may include acquiring an image including a first cell mass and a second cell mass different from the first cell mass, the analysis step may include determining a first parameter being the parameter for the first cell mass included in the image and a second parameter being the parameter for the second cell mass included in the image, and the evaluation step may include evaluating at least one of the first cell mass and the second cell mass based on a comparison of the first parameter and the second parameter.

In this way, by determining the first parameter for the first cell mass and the second parameter for the second cell mass and comparing them, the state of cells in the first cell mass and the state of cells in the second cell mass can be relatively evaluated. Therefore, for example, when the first cell mass and the second cell mass are cultured in the same container, it is possible to easily evaluate the degree of stability of the state of the plurality of cell masses being simultaneously cultured in the container.

Further, in the above state analysis apparatus, the imaging unit may acquire an image including a first cell mass and a second cell mass different from the first cell mass, and the analysis unit may determine a first parameter being the parameter for the first cell mass included in the image and a second parameter being the parameter for the second cell mass included in the image. Thus, it is possible to provide the state analysis apparatus capable of suitably performing the above evaluation method.

Further, the imaging step of the above evaluation method may include acquiring a first image including a first cell mass and a second image including a second cell mass different from the first cell mass, the analysis step may include determining a first parameter being the parameter for the first cell mass included in the first image and a second parameter being the parameter for the second cell mass included in the second image, and the evaluation step may include evaluating at least one of the first cell mass and the second cell mass based on a comparison of the first parameter and the second parameter.

Further, in the above evaluation method, the imaging step and the analysis step may be performed for a first cell mass, and a first parameter being the parameter for the state of the first cell mass may be determined, the imaging step and the analysis step may be performed for a second cell mass different from the first cell mass, and a second parameter being the parameter for the state of the second cell mass may be determined, and the evaluation step may include evaluating at least one of the first cell mass and the second cell mass based on a comparison of the first parameter and the second parameter.

In these ways, by determining the first parameter for the first cell mass and the second parameter for the second cell mass and comparing them, the state of cells in the first cell mass and the state of cells in the second cell mass can be relatively evaluated. Therefore, for example, when the first cell mass and the second cell mass are cultured in the same container, it is possible to easily evaluate the degree of stability of the state of the plurality of cell masses being simultaneously cultured in the container.

Further, the imaging step of the above evaluation method may include acquiring a first image including the cell mass at a first timing and acquiring a second image including the cell mass at a second timing after the first timing, the analysis step may include determining a first parameter being the parameter for the cell mass included in the first image and a second parameter being the parameter for the cell mass included in the second image, and the evaluation step may include evaluating the cell mass based on a comparison of the first parameter and the second parameter.

Further, in the above evaluation method, the imaging step and the analysis step may be performed at a first timing, and a first parameter being the parameter for the cell mass is determined, the imaging step and the analysis step may be performed at a second timing after the first timing, and a second parameter being the parameter for the cell mass is determined, and the evaluation step may include evaluating the cell mass based on a comparison of the first parameter and the second parameter.

In these ways, by comparing the plurality of parameters obtained at different timings for the same cell mass, it is possible to easily find the change with time of the state (or the fact that the state remains unchanged) of cells constituting the cell mass.

Further, in the above evaluation method and the state analysis apparatus, the light with which the cell mass is irradiated may be infrared light. Since light scattering in the cell mass is strong in the case of visible light, it is difficult to clearly image the vicinity of the center of the cell mass as the diameter of the cell mass increases. On the other hand, since light scattering in the cell mass is weak in the case of infrared light, it is possible to clearly image the whole region including the vicinity of the center of the cell mass even when the diameter of the cell mass is large (for example, 100 µm or more).

Further, the imaging step of the above evaluation method may include irradiating the cell mass crushed into a thin layer shape with the light from a thickness direction. Similarly, the above state analysis apparatus may further include a holding unit for holding the cell mass in a state of being crushed into a thin layer shape, and the cell mass may be irradiated with the light from a thickness direction. This makes it possible to thin the cell mass and to clearly image the whole region including the vicinity of the center of the cell mass.

INDUSTRIAL APPLICABILITY

The embodiments can be used as a cell mass evaluation method and a cell mass state analysis apparatus capable of more accurately evaluating a state of the cell mass based on an image.

REFERENCE SIGNS LIST

1A—state analysis apparatus, 3—light source, 5—holding unit, 5a—main portion, 5b—depressed portion, 5c—lid portion, 7—objective lens, 9, 13—reflecting mirror, 11—focusing lens, 15—imaging unit, 17—analysis unit, 19—evaluation unit, 21—computer, A, A1-A4—reference point, B—culture solution, C1-C9—sampling circle, CM, CM1-CM4—cell mass, CMa—contour, D, DD, D1-D4—image data, L1, L2—light, P1—first waveform.

The invention claimed is:

1. A cell mass evaluation method for evaluating a cell mass containing cells aggregated with each other, the method comprising:

an imaging step of capturing an image of light obtained from the cell mass by irradiation with light to the cell mass;

an analysis step of setting a reference point for the cell mass included in the image obtained by the imaging step, setting a sampling circle centered on the reference point, and determining a parameter for a state of the cell mass based on image data included in a region on the sampling circle; and an evaluation step of evaluating the cell mass based on the parameter, wherein the parameter is a width of a first waveform of an autocorrelation function of the image data along a circumferential direction of the sampling circle.

2. The cell mass evaluation method according to claim 1, wherein the parameter is a cell number density.

3. The cell mass evaluation method according to claim 1, wherein the cell mass is constituted by stem cells, and the evaluation step includes evaluating a degree of differentiation of the cell mass based on the parameter.

4. The cell mass evaluation method according to claim 1, wherein the analysis step includes setting a plurality of sampling circles having radii different from each other centered on the common reference point for the cell mass, and determining a plurality of parameters for the state of the cell mass based on the image data included in the regions on the plurality of sampling circles, and the evaluation step includes evaluating the cell mass based on a comparison of the plurality of parameters.

5. The cell mass evaluation method according to claim 1, wherein the imaging step includes acquiring an image including a first cell mass and a second cell mass different from the first cell mass, the analysis step includes determining a first parameter being the parameter for the first cell mass included in the image and a second parameter being the parameter for the second cell mass included in the image, and the evaluation step includes evaluating at least one of the first cell mass and the second cell mass based on a comparison of the first parameter and the second parameter.

6. The cell mass evaluation method according to claim 1, wherein the imaging step includes acquiring a first image including a first cell mass and a second image including a second cell mass different from the first cell mass, the analysis step includes determining a first parameter being the parameter for the first cell mass included in the first image and a second parameter being the parameter for the second cell mass included in the second image, and the evaluation step includes evaluating at least one of the first cell mass and the second cell mass based on a comparison of the first parameter and the second parameter.

7. The cell mass evaluation method according to claim 1, wherein the imaging step and the analysis step are performed for a first cell mass, and a first parameter being the parameter for the state of the first cell mass is determined, the imaging step and the analysis step are performed for a second cell mass different from the first cell mass, and a second parameter being the parameter for the state of the second cell mass is determined, and the evaluation step includes evaluating at least one of the first cell mass and the second cell mass based on a comparison of the first parameter and the second parameter.

8. The cell mass evaluation method according to claim 1, wherein
the imaging step includes acquiring a first image including the cell mass at a first timing and acquiring a second image including the cell mass at a second timing after the first timing,
the analysis step includes determining a first parameter being the parameter for the cell mass included in the first image and a second parameter being the parameter for the cell mass included in the second image, and
the evaluation step includes evaluating the cell mass based on a comparison of the first parameter and the second parameter.

9. The cell mass evaluation method according to claim 1, wherein
the imaging step and the analysis step are performed at a first timing, and a first parameter being the parameter for the cell mass is determined,
the imaging step and the analysis step are performed at a second timing after the first timing, and a second parameter being the parameter for the cell mass is determined, and
the evaluation step includes evaluating the cell mass based on a comparison of the first parameter and the second parameter.

10. The cell mass evaluation method according to claim 1, wherein the light with which the cell mass is irradiated is infrared light.

11. The cell mass evaluation method according to claim 1, wherein the imaging step includes irradiating the cell mass crushed into a thin layer shape with the light from a thickness direction.

12. A cell mass state analysis apparatus used for evaluating a cell mass containing cells aggregated with each other, the apparatus comprising:
a light source configured to output light with which the cell mass is irradiated;
an imager configured to capture an image of light obtained from the cell mass by irradiation with the light; and
an analyzer configured to set a reference point for the cell mass included in the image obtained by the imaging, set a sampling circle centered on the reference point, and determine a parameter for a state of the cell mass based on image data included in a region on the sampling circle, wherein
the parameter is a width of a first waveform of an autocorrelation function of the image data along a circumferential direction of the sampling circle.

13. The cell mass state analysis apparatus according to claim 12, wherein the parameter is a cell number density.

14. The cell mass state analysis apparatus according to claim 12, further comprising an evaluation unit configured to evaluate the cell mass based on the parameter determined by the analyzer.

15. The cell mass state analysis apparatus according to claim 14, wherein the cell mass is constituted by stem cells, and the evaluation unit is configured to evaluate a degree of differentiation of the cell mass based on the parameter.

16. The cell mass state analysis apparatus according to claim 12, wherein the analyzer is configured to set a plurality of sampling circles having radii different from each other centered on the common reference point for the cell mass, and determine a plurality of parameters based on the image data included in the regions on the plurality of sampling circles.

17. The cell mass state analysis apparatus according to claim 12, wherein
the imager is configured to acquire an image including a first cell mass and a second cell mass different from the first cell mass, and
the analyzer is configured to determine a first parameter being the parameter for the first cell mass included in the image and a second parameter being the parameter for the second cell mass included in the image.

18. The cell mass state analysis apparatus according to claim 12, wherein the light with which the cell mass is irradiated is infrared light.

19. The cell mass state analysis apparatus according to claim 12, further comprising a holder configured to hold the cell mass in a state of being crushed into a thin layer shape, wherein
the cell mass is irradiated with the light from a thickness direction.

20. A cell mass evaluation method for evaluating a cell mass containing cells aggregated with each other, the method comprising:
an imaging step of capturing an image of light obtained from the cell mass by irradiation with light to the cell mass;
an analysis step of setting a reference point for the cell mass included in the image obtained by the imaging step, setting a sampling circle centered on the reference point, and determining a parameter for a state of the cell mass based on image data included in a region on the sampling circle; and
an evaluation step of evaluating the cell mass based on the parameter, wherein
the parameter is a cell number density in the region on the sampling circle.

21. A cell mass state analysis apparatus used for evaluating a cell mass containing cells aggregated with each other, the apparatus comprising:
a light source configured to output light with which the cell mass is irradiated;
an imager configured to capture an image of light obtained from the cell mass by irradiation with the light; and
an analyzer configured to set a reference point for the cell mass included in the image obtained by the imaging, set a sampling circle centered on the reference point, and determine a parameter for a state of the cell mass based on image data included in a region on the sampling circle, wherein
the parameter is a cell number density in the region on the sampling circle.

* * * * *